United States Patent [19]
Sanberg et al.

[11] Patent Number: 5,942,437
[45] Date of Patent: Aug. 24, 1999

[54] METHOD AND MEDIA FOR ENHANCING VIABILITY MATURATION, AND CRYOPRESERVATION OF CELLS

[75] Inventors: Paul R. Sanberg, Spring Hill; Agneta Othberg, Tampa; Don F. Cameron, Lutz; Samuel Saporta, Tampa, all of Fla.; Cesario V. Borlongan, Silver Springs, Md.

[73] Assignee: University of South Florida, Tampa, Fla.

[21] Appl. No.: 08/799,108

[22] Filed: Feb. 11, 1997

Related U.S. Application Data

[63] Continuation-in-part of application No. 08/615,039, Mar. 12, 1996.

[51] Int. Cl.⁶ .................................................. A01N 63/00
[52] U.S. Cl. .......................... 435/374; 435/1.3; 435/347; 435/325; 424/93.7
[58] Field of Search .......................... 424/93.7; 435/325, 435/347, 374, 1.3

[56] References Cited

U.S. PATENT DOCUMENTS 5,082,670  1/1992  Gage et al. .............................. 424/520

FOREIGN PATENT DOCUMENTS

WO9528167  6/1995  WIPO .

OTHER PUBLICATIONS

Selawry et al., "Production of a factor, or factors, suppressing IL–2 production and T cell proliferation by sertoli cell–enriched preparations" *Transplantation* 52:846–850 (1991).

Beck et al. (1993) "The nature of the trophic action of brain–derived neurotrophic factor . . . " *Neurosci.*, 52:855–866.

Bellgrau (1995) "A role for CD95 ligand in preventing graft rejection" *Nature*, vol. 377, pp. 630–632.

Hynes et al., (1995) "Control of neuronal diversity by the floor plate: contact–mediated induction . . . " *Cell*, vol. 80, pp. 95–101.

Igdoura et al., (1996) "Trafficking of sulfated glycoprotein–1 (prosaposin) to lysosomes . . . " *Cell Tissue Res.*, 283:385–394.

Kleppner et al., (1995) "Transplanted human neurons derived from a teratocarcinoma cell line (NTera–2)" *J. Comp. Neurol.*, 357:618–632.

Knusel et al., (1990) "Selective and nonselective stimulation of central cholinergic and dopaminergic development . . . " *J. Neurosci.*, 10:558–570.

Knusel et al., (1991) "Promotion of central cholinergic and dopaminergic neuron differentiation by brain–derived . . . " *Proc. Natl. Acad. Sci. USA*, 88:961–965.

Kondoh et al., (1993) "Distribution of prosaposin–like immuno–reactivity in rat brain" *J. Comp. Neruol.*, 334:590–602.

Kordower et al., (1995) "Neuropathological evidence of graft survival and striatal reinnervation after the transplantation . . . " *New Engl. J. Med.*, 332:1118–1124.

Kordower et al., (1996) "Functional fetal nigral grafts in a patient with Parkinson's disease . . . " *J. Comp. Neurol.*, 370:203–230.

Kotani et al., (1996) "A hydrophilic peptide comprising 18 amino acid residues of the prosaposin sequence . . . " *J. Neurochem.*, 66:2197–2200.

Lindvall et al., (1990) "Grafts of embryonic dopamine neurons survive and improve motor function in Parkinson's disease" *Science*, 247:547–577.

Lindvall (1994) "Neural transplantation in Parkinson's disease" in *Functional Neural Transplantation* (S.B. Dunnett, A. Bjorklund, eds) Raven Press, Ltd., New York, pp. 103–137.

Martinez–Serrano et al., (1996) "CNS–derived neural progenitor cells for gene transfer of nerve growth factor to the adult brain . . . " *J. Neurosci.*, 15:5668–5680.

Mayer et al., (1993b) "Basic fibroblast growth factor promotes the survival of embryonic ventral mesencephalic . . . " *Neurosci.*, 56:379–388.

Bitgood et al., (1996) "Sertoli cell signaling by Desert hedgehog regulates the male germline" *Curr. Biol.*, 6:298–304.

Borlongan et al., (1997) "Intracerebral transplantation of testis–derived Sertoli cells in female rats . . . " *Cell Transplantation* (in press).

Bowenkamp et al., (1995) "Glial cell line–derived neurotrophic factor supports survival of injured midbrain DA neurons" *J. Comp. Neurol.*, 355:479–489.

Carson et al., (1984) "Synthesis and secretion of a novel binding protein for retinol by a cell line derived from Sertoli cells" *J. Biological Chemistry*, 269:3117–3123.

Chen et al., (1996) "The effect of prior in vitro exposure of donor cells to trophic factors in neurotransplantation" *Exp. Neurol.*, 138:64–72.

Choi–Lundberg and Bohn (1995)"Ontogeny and distribution of glial cell line–derived neurotrophic factor (GDNF) mRNA in rat " *Develop. Brain Res.*, 85:80–88.

Collard et al., (1988) "Biosynthesis and molecular cloning of sulfated glycoprotein–1 secreted by rat Sertoli cells . . . " *Biochemistry*, 27:4557–4560.

Engele and Bohn (1991) "The neurotrophic effects of fibroblast growth factors on dopaminergic neurons in vitro . . . " *J. Neurosci.*, 11:3070–3078.

(List continued on next page.)

*Primary Examiner*—Christina Y. Chan
*Assistant Examiner*—Patrick J. Nolan
*Attorney, Agent, or Firm*—Kohn & Associates

[57] ABSTRACT

A method to increase viability, number, survival and maturation of cells for transplantation or cryopreservation by culturing the cells with Sertoli cells or with sertoli–cell conditioned media (SCM) prior to transplantation (pre-culturing) or cryopreservation.

5 Claims, 9 Drawing Sheets

OTHER PUBLICATIONS

Freeman et al., (1995) "Bilateral fetal nigral transplantation into the postcommissural putamen in Parkinson's disease" *Ann. Neurol.*, 38:379–388.

Gash et al., (1996) "Functional recovery in parkinsonian monkeys treated with GDNF" *Nature*, 380:252–255.

Hiraiwa et al., (1992) "Binding and transport of gangliosides by prosaposin" *Proc. Natl. Acad. Sci. USA*, 89:11254–11258.

Hudson et al., (1995) "Glial cell line–derived neurotrophic factor augments midbrain dopaminergic circuits in vivo" *Brain Res. Bulletin*, vol. 36, No. 5, pp. 425–432.

Hyman et al., (1991) "BDNF is a neurotrophic factor for dopaminergic neurons of the substantia nigra" *Nature*, 350:230–232.

Mayer et al., (1993b) "Basic fibroblast growth factor promotes the survival of embryonic ventral mesencephalic . . . " *Neurosci.*, 56:389–398.

Miao et al., (1996) "A neurotrophic activity of sonic hedgehog promotes the survival of dopaminergic neurons" *Cell Transplant.*, 5S–2,17. (abstract).

Morales et al., (1996) "Expression and tissue disribution of rat sulfated glycoprotein–1 (Prosaposin)" *J. Histochem. Cytochem.*, 44:327–337.

Nikkhah et al., (1993) "Platelet–derived growth factor promotes survival of rat and human mesencephalic dopaminergic . . . " *Exp. Brain Res.*, 92:516–523.

O'Brien et al., (1994) "Identification of prosaposin as a neurotrophic factor" *Proc. Natl. Acad. Sci. USA*, 91:9593–9596.

O'Brien et al. (1985) "Identification of the neurotrophic factor sequence of prosaposin" *FASEB*, 9:681–685.

Olson (1996) "Toward trophic treatment in parkinsonism" a primate step *Nature Med.*, 2:400–401.

Othberg et al., (1995) "Specific effects of platelet derived growth factor (PDGF) on fetal rat and human DA neurons . . . " *Exp. Brain Res.*, 105:111–122.

Pleasure and Lee (1993) "NTera 2 cells: a human cell line which displays characteristics expected of a human . . . " *J. Neurosci. Res.*, 35:585–602.

Poulsen et al., (1994) "TGFβ2 and TGFβ3 are potent survival factors for midbrain dopaminergic neurons" *Neuron*, 13:1245–1525.

Rosenblad et al., (1996) "Glial cell line–derived neurotrophic factor increases survival, growth and function . . . " *Neurosci.*, 75:979–985.

Sanberg et al., (1996) "Testis–derived Sertoli cells survive and provide localized immunoprotection for xenografts in rat brain" *Nature Biotech.*, 14:1692–1695.

Sauer et al., (1995) "Glial cell line–derived neurotrophic factor but not transforming growth factor β3 prevents delayed degeneration . . . " *Proc. Natl. Acad. Sci. USA*, 92:8935–8939.

Sauer and Brundin (1991) "Effects of cool storage on survival and function of intrastriatal ventral mesencephalic grafts" *Restor. Neurol. Neurosci.*, 2:123–135.

Skinner (1993) "Secretion of growth factors and other regulatory factors" in *The Sertoli Cell*, Rusell, L.D. and Griswold, M.D., eds Cache River Press, Clearwater, Florida, pp. 237–248.

Stromberg et al., (1993) "Glial cell line–derived neurotrophic factor (GDNF) is expressed in the developing but not adult straitum . . . " *Exp. Neurol.*, 124:401–412.

Takayama et al., (1995) "Basic fibroblast growth factor increases DA graft survival and function in a rat model . . . " *Nature Med.*, 1:53–58.

Yoshimoto et al., (1995) "Astrocytes retrovirally transduced with BDNF elicit behavioral improvement in a rat model . . . " *Brain Res.*, 691:25–36.

Zurn et al., (1994) "Glial cell line–derived neurotrophic factor (GDNF), a new neurotrophic factor for motoneurones" *NeuroReport*, 6:113–118.

Hedger (1989) "The testis: an 'immunologically suppressed' tissue?" *Reprod. Fertil. Dev.*, 1:75.

Takayama et al. (1995) Basic fibroblast growth factor increases dopaminergic graft survival and function . . . *Nature Medicine*, 1:53–58.

Berden et al., "Severe central–nervous system toxicity associated with cyclosporin" *The Lancet* 26:219–220 (1985).

Bjorklund and Stenevi, "Intracerebral neural grafting: A historical perspective" *Neural grafting in the mammalian CNS*, Amsterdam:Elsevier pp. 3–14 (1985).

Bjorklund, "Dopaminergic transplants in experimental parkinsonism: cellular mechanisms of graft–induced functional recovery" Current Biology, 2:683–689 (1992).

Borlongan et al., "Cyclosporine–a increases spontaneous and dopamine agonist–induced locomotor behavior in normal rats" *Cell Transplantation*, vol. 4, No. 1, pp. 65–73 (1995).

Borlongan et al., "Striatal dopamine–mediated motor behavior is altered following occlusion of the middle cerebral artery" *Pharm. Biochem. and Behavior*, vol. 52, No. 1 pp. 225–229 (1995).

Borlongan et al., "Systemic 3–nitropropionic acid: behavioral deficits and striatal damage in adult rats" *Brain Research Bulletin* vol. 36, No. 6, pp. 549–556 (1995).

Cameron et al., Sertoli cells maintain spermatid viability in vitro" *Cell biology of the testis and epididymis*, vol. 513 Annals of the New York Academy of Sciences, pp. 419–423 (1987a).

Cameron et al., "Alterations of androgen–binding protein (ABP) in sertoli/spermatid cocultures with varying . . . " *Cell biology of the testis and epididymis*, New York Acad. Sci., pp. 448–451 (1987b).

Cameron et al., "Successful islet/abdominal testis transplantation does not require leydig cells[1]" *Transplantation*, vol. 50, No. 4 pp. 649–653 (1990).

Cameron and Muffly, "Hormonal regulation of spermatid binding" *Journal of Cell Science*, 100:623–633 (1991).

de Groen et al., "Central nervous system toxicity after liver transplantation" *The New England Journal of Medicine*, 14:861–866 (1987).

Freeman et al., "The USF protocol for fetal nigral transplantation in Parkinson's Disease" *Experimental Neurology*, 129:6–7 (1994).

Griswold, Protein secretion by sertoli cells: general considerations Russel, L.D. and M.D. Griswold, eds. The Sertoli Cell, Cache River Press, Clearwater, Fl., pp. 195–200 (1992).

Isacson et al., "Graft–induced behavioral recovery in an animal model of huntington disease"*Proc. Natl. Acad. Sci. USA*, vol. 83, pp. 2728–2732 (1986).

Koutouzis et al., "Intrastriatal 3–nitropropionic acid: a behavioral assessment" *NeuroReport*, vol. 5, No. 17 pp. 2241–2245 (1994).

Koutouzis et al., "Systemic 3–nitropropionic acid: long–term effects on locomotor behavior" *Brain Research*, 646:242–246 (1994).

Lindvall et al., "Transplantation in parkinson's disease: two cases of adrenal medullary grafts to the putamen" *Annals of Neurology* vol. 22, No. 4, pp. 457–468 (1987).

Lindvall et al., "Grafts of fetal dopamine neurons survive and improve motor function in parkinson's disease" *Science*, 247:574–577 (1990).

Pakzaban et al., "Increased proportion of acetylcholinesterase–rich zones and improved morphological integration in host striatum of . . . ", *Brain Research*, 97:13–22 (1993).

Sagen et al., "Transplants of immunologically isolated xenogeneic chromaffin cells provide a long–term source of pain–reducing . . . " *Journal of Neuroscience*, 13:2415–2423 (1993).

Sanberg et al., "Transplantation into the central nervous system" R.G. Landesd Co., Boca Raton, Fl., pp. 19–21 (1994).

Selawry and Cameron, "Sertoli cell–enriched fractions in successful islet cell transplantation" *Cell Transplantation*, vol. 2, No. 3 pp. 123–129 (1993).

Wictorin et al., "Reformation of long axon pathways in adult rat central nervous system by human forebrain neuroblasts" *Nature*, vol. 347, pp. 556–558 (1990).

METHOD AND MEDIA FOR ENHANCING VIABILITY MATURATION, AND CRYOPRESERVATION OF CELLS

This application is a Continuation-In-Part of U.S. Ser. No. 08/615,039, filed Mar. 12, 1996.

BACKGROUND OF THE INVENTION

1. Technical Field

The present invention generally relates to cell transplantation and specifically to methods of improving cell viability, graft survival, the viability of cryopreserved cells and providing increased numbers of differentiated cells for transplant.

2. Background Art

Transplantation of cells and tissues is being utilized therapeutically in a wide range of disorders from cystic fibrosis (lungs), kidney failure, degenerative heart diseases to neurodegenerative disorders. Improved means to facilitate such transplants are needed, particularly where differentiated cells are being transplanted. Generally these cells cannot be cultured to increase cell number so preservation of viability for transplant is critical. Further, the number of differentiated cells available for transplant is often low and methods of increasing the number and/or availability of such cells are also needed.

Transplantation protocols in addition to transplanting tissues and/or organs can include the infusion of cell suspensions from a donor. A wide range of transplantable material either currently being transplanted or contemplated for transplants includes skin grafts, corneas, hepatic tissue, kidneys, hearts, islet cells, neurons, bone, bone marrow, and the like. The obligatory step for the success of this kind of treatment is to have enough viable cells or organs a available for the transplant.

For example, in some cancer therapies a patient's bone marrow is removed, and then reinfused following high dose chemo- and/or radiation therapies. It would be useful to have improved methods of preserving such autologous cells. In other cases, bone marrow must be from donors. Often there is not a match from relatives and the marrow must be matched from the national registry. It would be useful to be able to have preserved such cells rather than having to find the donor at the time the cells are needed. Therefore, improved methods of cryopreservation are needed since a substantial portion of cryopreserved cells are not viable upon thawing.

In addition, hybridomas are stored utilizing cryopreservation. Improved methods for preserving hybridomas with increased viability would be useful.

As a further example, the central nervous system (CNS) (brain and spinal cord) has poor regenerative capacity which is exemplified in a number of neurodegenerative disorders. An example of such a disorder is Parkinson's disease. The preferred pharmacotherapy for Parkinson's disease is L-dopa which helps the symptoms of this disease in humans. However, the neuropathological damage and the debilitating progression is not reversed by this pharmaceutical treatment protocol.

Laboratory and clinical studies have shown the transplantation of cells into the CNS is a potentially significant alternative therapeutic modality for neurodegenerative disorders such as Parkinson's disease (Wictorin et al., 1990; Lindvall et al., 1990; Sanberg et al., 1994; Bjorklund and Stenevi, 1985; Freeman et al., 1994). In some cases, transplanted neural tissue can survive and form connections with the CNS of the recipient, i.e. the host (Wictorin et al., 1990). When successfully accepted by the host, the transplanted cells and/or tissue (i.e.. the graft) have been shown to ameliorate the behavioral deficits associated with the disorder (Sanberg et al., 1994). The obligatory step for the success of this kind of treatment is to have enough viable cells available for the transplant.

Currently, fetal neural tissue is the primary graft source for neural transplantation (Lindvall et al., 1990; Bjorklund, 1992; Isacson et al., 1986; Sanberg et al., 1994). Other viable graft sources include adrenal chromaffin cells and various cell types that secrete neural growth factors and trophic factors. The field of neural tissue transplantation as a productive treatment protocol for neurodegenerative disorders has received much attention resulting in its progression to clinical trials. Preliminary results and clinical observations are promising but obtaining enough viable cells remains a problem.

For example, one treatment for Parkinson's disease (PD) intracerebral transplantation therapy, has accentuated research interest in restoring some of the circuits in the nigrostriatal pathway [Lindvall et al., 1990; Lindvall, 1994; Freeman et al., 1995; Kordower et al., 1995, 1996]. While the initial findings are encouraging and have resulted in behavioral improvements in patients with PD, the current clinical protocols for intracerebral transplantation have to be improved in terms of increasing short- and long-term survival of embryonic dopaminergic (DA) cells, and to find alternative graft sources to avoid the problem with lack of donor tissue obtained from elective abortions.

Lately, research has focused on finding trophic factors, able to increase the survival of DA cells prepared for transplantation, maintain the in situ survival post-transplantation of embryonic DA neurons transplanted into the striatum, as well as increase graft volume, and thereby re-innervate a larger part of the caudate and putamen which has been shown to have effect both in vitro and in vivo. Trophic factors such as NGF, bFGF, EGF, IGF I and II, TGFβ1-3, PDGF, BDNF, and GDNF [Engele and Bohn, 1996; Mayer et al., 1993; Knusel et al., 1990, 1991; Poulsen et al., 1996; Nikkhah et al., 1993; Othberg et al., 1995; Hyman et al., 1991, 1993; Lin et al., 1993] have been investigated and shown to have pronounced effects in vitro, however the effects in vivo have yet to be further established. Reversal of MPTP and 6-OHDA lesions in primates [Gash et al., 1996] and rats, as well as increased graft survival, have been demonstrated by the addition of NGF or bFGF to the cell suspension prior to grafting [Chen et al., 1996; Dunnett et al., 1995], or by transplanting neurons derived from a neural progenitor (CINP) cell line, transduced retrovirally with NGF [Martinez-Serrano et al., 1995] and astrocytes transduced with BDNF [Yoshimoto et al., 1996]. GDNF has been shown to increase graft survival, extend fiber outgrowth and alleviate behavioral effects after 6-hydroxydopamine lesions in the striatum of rats [Sauer et al., 1994; Johansson et al., 1995; Bowenkamp et al., 1995; Rosenblad et al., 1996; Olson, 1996].

In treating disease it is often useful to treat tissue locally, rather than systemically, with trophic factors, particularly areas of tissue damage as for example in wound healing. Additionally, it is becoming increasingly recognized that multiple trophic factors acting in concert are likely to be necessary for successful treatment. Further, the availability of multiple trophic factors at various time points during treatment may be necessary to enhance successful treatment.

Long term maintenance of functional recovery has been observed in a diabetic animal model utilizing a novel transplantation treatment protocol utilizing isolated islet cells and Sertoli cells. It is clear that the efficacy of the treatment is due to the presence of the Sertoli cells, in part, due to their known immunosuppressive secretory factor. (Selawry and Cameron, 1993; Cameron et al., 1990). However, Sertoli cells are also known to secrete a number of important trophic growth factors.

Accordingly, it would be desirable to utilize Sertoli cells as a source for trophic factors to improve viability and growth of cells/tissues for transplantation, cryopreservation and for trophic factor support of damaged tissue. Sertoli cells actively participate in the genesis of spermatozoa. The Sertoli cells make a wide variety of nutritive, trophic and regulatory proteins, amongst them a wide variety of trophic factors and their receptors [Skinner, 1993]. Individual trophic factors, as listed in Table 1, have been evaluated, but biological requirements are complex and the interaction of various components often necessary to effectively provide the necessary stimulants. It would be useful to design preparations that provide the various components and interactions to effectively improve viability, maturation, number and growth of cells/tissues for transplantation and for wound healing and cryopreservation.

Cell transplantation therapies are optimized by the availability of cryopreserved cells which have high viability. Transplantable cells, such as fetal brain cells, do not withstand cryopreservation well. Therefore, it would be desirable to have a method for enhancing the preservation and viability of cryopreserved cells in order to optimize the function of the cells and to obtain the resultant benefits to the transplant recipient.

SUMMARY OF THE INVENTION AND ADVANTAGES

In accordance with the present invention, there is provided a method of enhancing the viability of cryopreserved cells including the steps of culturing Sertoli cells in media to produce Sertoli-cell conditioned media (SCM), adding the conditioned media to cells to be cryopreserved and then cryopreserving the cells.

In a further embodiment, the method includes the steps of co-culturing Sertoli cells and cells to be cryopreserved and then cryopreserving the cells.

Also in accordance with the present invention, there is provided a medium for enhancing the viability, maturation and cryopreservation of cells. The medium is generated by the steps of culturing Sertoli cells in media to produce Sertoli cell conditioned medium (SCM) and removing the SCM from the Sertoli cells.

The present invention also provides a method to increase survival and maturation of cells for transplantation by the step of culturing the cells with Sertoli cells or with sertoli-cell conditioned media.

Also in accordance with the present invention a method of improving survival of a graft in situ by treating the graft in situ with sertoli-cell conditioned media or Sertoli cells is provided. Also the method of the present invention can be use to improve wound healing in situ by treating the wound in situ with sertoli-cell conditioned media.

The method of the present invention provides a means to induce phenotypic change in cells for transplantation by culturing the cells to be transplanted with sertoli cells or conditioned sertoli cell media.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1A:
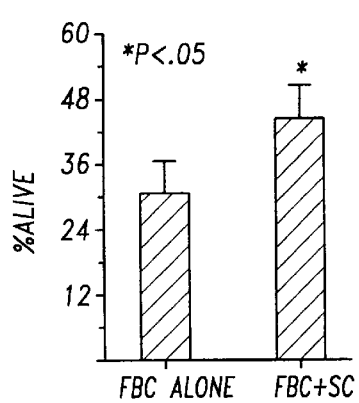
FIGS. 1A–E are bar graphs illustrating the viability of post thaw cryopreserved (A) rat fetal brain cells (FBC) cryopreserved with rat Sertoli cells, (B) rat fetal brain cells (FBC) cryopreserved with porcine Sertoli cells, (C) hNT cells cyropreserved with porcine Sertoli cells and (D) the effect on the number of cells, (E) increased survival of post-thaw co-cryopreserved E15 Tyrosine hydroxylase positive dopaminergic neurons and rat Sertoli cells, the number of live vs. dead cell estimates were made one hour following thawing, * denotes p<0.05 with Students t-test.

The present invention provides a method to increase viability, number, survival and maturation of cells for transplantation or cryopreservation by culturing the cells with Sertoli cells or with sertoli-cell conditioned media (SCM) prior to transplantation (pre-culturing) or cryopreservation.

By use of the term cells it can include tissue including organs as well as suspensions of separated cells as will be apparent from the text. The cells or tissue upon transplantation can be referred to as a graft. The cells for transplantation can include but are not limited to islets cells for diabetes; myoblasts for muscular dystrophy; human or animal neurons for stroke, brain and spinal cord injury, Alzheimer's disease, Huntington's disease and other neurodegenerative disorders; septal and GABAergic cells for epilepsy; chromaffin, ventral mesencephalic or other dopaminergic cells for treatment of Parkinson's Disease; trophic factor secreting cells for neurological disorders; hepatocytes for liver disease; skin grafts for wound healing and/or burns, and bone marrow or stem cells for hematopoietic and genetic disorders.

The method of the present invention can be utilized with transplantable cells from tissues such as endocrine cells, muscle cells, and other cells by utilizing similar techniques as those described herein for neural cells. Furthermore, the method of the present invention may be used for enhancing the outcomes of cell transplant, such as myoblast transplants and cells for gene therapy, by providing such cells with enhanced viability and tropic support for transplant. That is, Sertoli cells and the trophic factors which they produce and/or secrete into the conditioned media are used to facilitate cell viability and maturation and transplant survival and graft function of the cells being transplanted.

Further, the present invention provides in an embodiment that the cells to be transplanted are dopaminergic neuronal cells which are generally of fetal or embryonic origin as discussed herein above for Parkinson's disease. In a further embodiment the absolute number of dopaminergic neural cells in culture is increased utilizing the method of the present invention from a human teratocarcinoma cell line as shown in the Examples.

Maturation of the cells to be transplanted includes differentiation of the cells and can include changes in density of cell surface receptors as well as induction, distribution and quality of cell surface receptors and other markers of cell activity. This can be referred to as a change in phenotype of the cell. These changes will be dependent on the type of cell being cultured and can include changes in phenotype in addition to cell surface receptors. For example, for neural cells the phenotypic changes can include prolongation of axons and neurite outgrowth, changes in pattern of neurite branching, changes in number of growth cones and processes, changes in synaptic transmitter substances and nuclear shape as shown in the Examples.

As discussed herein, there is a need for differentiated viable cells for transplantation. The method of the present invention, by culturing with sertoli cell conditioned media or with sertoli cells allows for the maturation, i.e.change in phenotype, of the cells so that adequate numbers of differentiated cells are available for transplantation.

The present invention also provides methods for enhancing the viability of cryopreserved cells by culturing Sertoli cells or Sertoli-cell conditioned medium with the cells to be cryopreserved. Alternatively, the method of the present invention provides for adding the conditioned medium to cryopreserved cells upon thawing.

Enhanced viability describes the ability of cells to survive and function normally following a sustained period of cryopreservation. This can also be referred to as post-thaw viability. That is, cells which are harvested and cryopreserved for later use for purposes including transplantation, can be thawed and a greater percentage of the cells will be alive and viable retaining their original functions. For example, differentiated, non-dividing cells can be harvested for transplantation, cryopreserved according to the present invention, and thawed resulting in a substantially greater percentage of live cells than by previous methods of cryopreservation.

By cryopreserved or cryopreservation, it is meant that the cells are stored at temperatures which are low enough to prevent normal biological functions from occurring. Generally this temperature is at least $-70°$ C. and lower under liquid nitrogen. At these low temperatures, biological degradation of the cells is inhibited thereby preserving the functions of the cells. However, as described above, the prior art methods of cryopreserving cells result in a substantial proportion of cells failing to survive or be viable following cryopreservation. Typically, cryopreservation involves storing cells in a medium which may contain DMSO or an equivalent at very low temperatures by refrigeration or storage under liquid nitrogen or other types of cooling, as known to those skilled in the art.

The cells which may be cryopreserved with Sertoli cells or in SCM, according to the present invention, include but are not limited to cells of the peripheral and central nervous system including neural cells, lymphocytes, hybridomas, fibroblasts, cells for gene therapy, fetal cells from various tissues, myoblasts, hepatocytes, endocrine cells, endothelial cells and the like.

As shown in the Examples herein below, the cells preserved or produced in accordance with the present invention can be transplanted into the CNS (brain) to replace dysfunctional cells and when co-transplanted with Sertoli cells, can avoid being rejected. Such a protocol results, therefore, in increased cell survival and cell functional integration with the host tissue. This then will promote re-establishment of normal neural tissue function and thereby ameliorate the behavioral and functional deficits associated with the neurological and/or neurodegenerative disorder being treated.

The present invention also provides a method of producing a sertoli-cell conditioned medium (SCM). The source of Sertoli cells is by primary cell isolation from the mammalian testis. The protocol for harvesting the cells is as set forth by Cameron and Muffle (1991) and by Griswold (1992). The method of the present invention can be used with Sertoli cells from any suitable mammalian source such as rat or porcine. However, if available and suitable, human Sertoli cells may be utilized.

The conditioned medium is prepared by culturing Sertoli cells in a suitable culture medium (incubation medium) as described herein. Isolated Sertoli cells are cultured in incubation medium from one hour to seven days and at a cell density of $1\times10^4$ to $1\times10^7$ cells/cm$^2$ at 39° C. with 5%$CO_2$–95% air. In a preferred embodiment the isolated Sertoli cells are cultured in incubation media for 48 hours at a density of $6\times10^5$/cm$^2$ and at 39° C. with 5%$CO_{2-95}$% air. It should be noted that time versus cell density as well as culture temperature can be adjusted in determining the culture conditions can be adjusted as known to those skilled in the art such that the conditioned media is standardized between species as needed.

Following incubation of the Sertoli cells in the incubation medium, the medium (SCM) is deemed "conditioned". That is, following the conditioning of the medium, the medium contains nutritional, immunosuppressive, and other factors from Sertoli cells defined herein as trophic factors which enhance not only the viability of cells, but which imparts enhanced growth characteristics and can induce changes in phenotype to the cells cultured in the conditioned medium. The Sertoli cells are generally removed from the conditioned media of the present invention following the culturing of the Sertoli cells therein.

For cryopreservation, the Sertoli cells can be removed from the conditioned media of the present invention following the culturing of the Sertoli cells therein, or, can be left in the conditioned media to further enhance the cells to be cryopreserved. Additionally, the cells to be cryopreserved can be co-cultured with the Sertoli cells prior to cryopreservation. Furthermore, the conditioned medium containing the trophic factors can be added to other media for cell culturing and cryopreservation.

In general the incubation media used to culture the sertoli cells is as set forth in the Examples herein below and after an initial culture with serum-containing media (as indicated in the text) the incubation media during the final culture is a serum-free media. However, where appropriate for human use or veterinary use the initial culture may be with species specific serum. In an embodiment the serum-free media is either X vivo-10 or X vivo-15 media (Whittaker Bioproducts). This is a serum-free and FDA-approved media for IL-2/LAK infusions in patients.

Following incubation the conditioned media is collected. Matched species serum albumin can be added to stabilize the conditioned media if necessary. The conditioned media is stored at 4° C. to −70° C., depending on when it will be used.

The present invention provides for a conditioned media in a preferred embodiment produced by culturing sertoli cells in a serum-free culture media for 48 hours and at a cell concentration of $6 \times 10^5$ cells/cm$^2$ or alternatively in a combination of time and cell density providing the same conditioned media. The conditioned media is standardized by bioassay. In general cells of interest are cryopreserved and/or observed for changes in phenotype in each lot of the conditioned media. The conditioned media must provide the same post-thaw viability, cell number increase or phenotypic changes as have been determined for the initial use of the conditioned media.

The conditioned media is further characterized by measuring the trophic factor content by bioassay and appropriate immunoassays or other assays. Sterility is tested by culture in thioglycolate broth and endotoxin measured by limulus lysate assay as is known in the art. Where necessary DNA and virus exclusion, if needed, will employ such techniques as ultrafiltration, column chromatography, virasol, ethanol fractionation, polyethylene glycol/bentonite precipitation, gamma irradiation, and/or solvent/detergent treatment as has been used for intravenous gamma globulin and monoclonal antibodies. Each lot of conditioned media is standardized either by concentration or amount administered so that comparisons can be made.

The present invention also provides a method of improving survival of a graft in situ by treating in situ with sertoli-cell conditioned media, generally at the time of transplant and can also include the use of Sertoli cells as appropriate. The method also encompasses improving wound healing in situ by treating in situ with sertoli-cell conditioned media either topically or by site-directed injection. In an embodiment the wound to be treated is an injured spinal cord, brain or skin wound.

The conditioned media utilized in the present invention, is administered in combination with other drugs or singly consistent with good medical practice. The composition is administered and dosed in accordance with good medical practice taking into account the clinical condition of the individual patient, the site and method of administration, scheduling of administration, and other factors known to medical practitioners. The "effective amount" for purposes herein is thus determined by such considerations as are known in the art. The amount must be effective to achieve improvement including but not limited to prolonged graft survival or improved wound healing rate or length and other indicators as are selected as appropriate measures by those skilled in the art.

The present invention provides a method to induce phenotypic change in cells for transplantation by culturing the cells to be transplanted with sertoli cells. The cells are pre-cultured with the sertoli cells in a culture media for seven days and at a cell concentration of $1 \times 10^5$ cells/cm$^2$ for the cells to be transplanted and at a cell concentration of $2.5 \times 10^5$ cells/cm$^2$ for the sertoli cells. The cells to be transplanted are then harvested, isolated and transplanted. Adjustments in culture conditions as are known to those skilled in the art to accommodate species differences can be made.

In an embodiment as shown in the Examples, the method utilizes cells from a human teratocarcinoma neuronal cell line and using the method of the present invention the absolute number of tyrosine hydroxylase positive neurons in the culture is increased. This method thereby increases the absolute number of dopaminergic neural cells available for transplant.

Utilizing fetal rat ventral mesencephalic neurons (VM) and human postmitotic neurons (hNT) derived from a cell line applicants demonstrate in the Examples herein below that culturing such cells with Sertoli cells or Sertoli cell conditioned media enhanced survival of fetal dopamine neurons and it increased neuritic outgrowth and cell body area as well as increasing post-thaw viability after cryopreservation.

Further, it was unexpected found in culturing the hNT cells that the absolute number of dopamine neurons (tyrosine-hydroxylase, TH, positive) increased. The culture conditions with the Sertoli cells or Sertoli cell conditioned media changed the phenotype of neurons in the culture to be dopamine neurons.

As shown in the Examples the survival of neurons is promoted by the stimulation of direct co-culture with Sertoli cells or sertoli cell conditioned media, which have a direct trophic effect on soma size, neurite outgrowth and can cause a change of phenotype in vitro. The average TH-positive cell number, and measurements of soma size, neurite outgrowth and number of branching points of the embryonic DA neurons treated with Sertoli cell co-culture, or culture in Sertoli cell conditioned media, were significantly increased after 7 days in vitro.

These data suggest that Sertoli cells can provide a constant secretion of trophic support, important for the survival and maturation of embryonic DA neurons in vivo. The change of phenotype seen in the human cell line, also provide additional support that certain proteins or gene products secreted by non-CNS Sertoli cells play an important role for development and maturation of the CNS.

Moreover, the phenotypic change as seen by the induced increased number of TH-positive neurons in the hNT-neuronal co-cultures were also seen with rat VM cells in Sertoli cell co-culture. The cells responded in co-culture in a ratio-dependent manner and the optimal ratios for VM cells were 1:5–1:1 (Sertoli:VM) and for hNT neurons, the ratio 5:1 (SC:hNT) was most potent.

A hypothesis for the above observations can be made, but it is not to be construed as limiting the present invention to this one mode of action. An early viability decline in the VM cell preparation may be a crucial factor for the poor survival of such transplants in the clinical intracerebral grafting protocols in Parkinson's disease (PD) treatment. It is therefore important to improve the in vitro cell viability in order to yield a higher number of surviving DA neurons which could expand the reinnervation of the striatum by increasing graft survival.

Continuing improvement has been seen only in PD patients receiving at least 3 to 4 embryonic VMs per side of the brain [Lindvall, 1994; Freeman et al., 1995]. The large number of embryonic donors required per patient is due to the fact that only 5–20% of the DA neurons survive [Sauer and Brundin, 1991; Kordower et al., 1996] the implantation. The cause of the poor survival may be due to the initial tissue dissection could produce axotomy of DA neurons, which might lead to retrograde cell death. Moreover, the long term underlying disease process in PD, may cause detrimental challenges on the transplanted DA neurons and an allograft immune response which could induce a rejection of the transplanted cells. Therefore, if this damage is reduced, it should increase survival of transplanted DA neurons.

Although many trophic factors have been reported to have an effect on DA neurons in vitro, there has only been a few successful reports about the in vivo effects of growth factors. The dilemma with long-term administration of trophic factors has been approached by either generating trophic factor secreting cells [Yoshimoto et al., 1995; Martinez-Serrano, 1996], or by adjunction of neurotrophins into different matrixes such as GDNF in fibrin glue [Johansson et al., 1995], and hence be able to provide neurotrophic secretion in vivo. However, there is still no evidence for effects of long-term administration, which will be preferable to be able to support transplanted tissue in the brain. The fact that rat and porcine Sertoli cells have effect on survival and maturation of both rat VM neurons and hNT neurons, support Applicants earlier findings that it is possible to co-transplant neurons and Sertoli cells into the brain. The Sertoli cells can survive in the brain and provide for a life-time secretion of trophic factors and locally induced immunosuppressive factors.

The desert hedge hog (dhh) gene plays an important role in pattern formation of embryonic structures and has been shown to be present in developing and mature Sertoli cells [Bitgood et al., 1996]. It has also been shown that the hedgehog gene family has had a substantial effect on survival of DA neurons in vitro [Miao et al., 1996]. This suggests that Sertoli cells can induce an up-regulation of the dhh gene in the DA neurons and thus increase trophic factor secretion.

Prosaposin has been shown to be present in rats at birth and increase gradually in brain contents after postnatal day 10 when synaptogenesis begins to take place [Kotani et al., 1989]. It has been demonstrated that Sulfated glycoprotein-1 (SGP-1), homologous to Prosaposin in rat Sertoli cells, is released at specific stages of spermatogenesis [Collard et al., 1988], and have been proposed to be secreted by lysosomes [Igdoura et al., 1996]. Prosaposin has been detected in adult brain and testis by Northern blot analysis [Morales et al., 1996]. The trophic properties of Prosaposin has been demonstrated on murine and human neuroblastoma cells in vitro [O'Brien et al., 1994] showing neuritic outgrowth. Recently, studies of hippocampal CA1 neurons, have demonstrated that prosaposin has effect on rescuing those neurons after ischemic insult both in vitro and in vivo [Kotami et al., 1996].

Sertoli cell secreted trophic factors are potent for increased survival and morphological changes in vitro, and should, therefore provide an unique in situ long term delivery of trophic molecules when co-transplanted with embryonic DA cells or with other grafts.

The present invention provides in one embodiment for the co-culturing of Sertoli cells and a second cell type to be cryopreserved in media and cryopreserving the co-cultured cells together. Upon thawing, the Sertoli cells are therefore present and would be co-transplanted with the second cell type. Such a co-cellular transplant provides additional advantages.

Sertoli cells provide local immunosuppression by secreting an immunosuppressant agent, so that there would be no successful antibody or cellular immunological attack waged against the transplanted cells, including the Sertoli cells themselves. Additionally, since the immunosuppression is local and by a biologically tolerable agent, the side effects associated with both systemic immunosuppression and cytotoxicity of agents such as CsA would be avoided. Hence, Sertoli cell co-transplantation provides a significant improvement over the use of systemic immunosuppression with CsA as the necessary adjunctive therapy to neural transplantation as shown in the example below.

The localized immunosuppression by a Sertoli cell-derived immunosuppressant agent can facilitate the survival of both cellular xenografts and allografts. With allografts, co-transplantation with Sertoli cells should provide localized immunosuppression so as to eliminate the need for systemic immunosuppression. With xenografts, co-transplantation with Sertoli cells can provide sufficient local immunosuppression so as to eliminate the need for systemic immunosuppression or the Sertoli cells may be used in combination with a systemic immunosuppressant at a lower dose to prevent rejection. When co-transplanted, the Sertoli cells not only provide local immunosuppression but provide trophic support (i.e. regulatory, nutritional and other factors) to the co-transplanted cells (i.e. the graft). Therefore, the Sertoli cells will not only provide inhibition of the immune response, but will allow enhanced growth and viability of allografts and xenografts by concomitant trophic support.

The above discussion provides a factual basis for the use of sertoli-cell conditioned medium and Sertoli cells for preculturing cells to be transplanted prior to transplantation to increase survival and maturation and for cryopreservation. The methods used with and the utility of the present invention can be shown by the following examples.

EXAMPLES

General Methods

Rat embryonic ventral mesencephalic and porcine Sertoli cell co-cultures: Tissue to obtain ventral mesencephalon (VM) was collected from time pregnant rats, embryonic day 15 (E15; Civic Miller). The litter, after removal of the amnion, was placed into Hank's balanced salt solution (HBSS; Life Technologies) +15 mM Hepes (Life Technologies). The CNS was dissected out and VM was localized and divided along the midline and a cell suspension was prepared as described earlier [Othberg et al., 1995]. Briefly, the tissue was chemically dissociated in 0.1% trypsin (Sigma) and 0.05% deoxyribonuclease (Dnase;

Sigma) in HBSS+15 mm Hepes 20 minutes at 37° C. The trypsin was removed and the tissue was rinsed 5 times in 0.05% DNase followed by a mechanical dissociation by the use of 1 ml automatic pipette into a single cell suspension. The cell number was estimated by a trypan blue dye exclusion method and was thereafter seeded at a concentration of 100,000 cells/cm$^2$, in poly-L-lysin (Sigma; 10 μg/ml) coated 48 well plates (Costar). The cells were plated in plating medium (DMEM:F12 supplemented with 3 mg/ml L-glutamine (Sigma), 0.01 ml/ml gentamicin sulfate (Gibco), 50 ng/ml retinol (Sigma), and 0.01 ml/ml insulin-transferrin-selenium (ITS, Collaborative Research, Inc.))

The dose/ratio response curve was performed by mixing porcine Sertoli cells:VM cells in the following ratios: 1:100, 1:10, 1:2.5, 1:1, 2.5:1, 5:1. The control for the dose-response was no Sertoli cells and 100,000 VM cells/cm$^2$ in medium as described. Applicants used either freshly isolated or cryopreserved porcine Sertoli cells in the dose response study.

hNT neuron and culture: The hNT cell line (Stratagene®, catalog number 204104) is derived from a human teratocarcinoma cell line (NT2), induced by retinoic acid to differentiate in vitro into postmitotic neurons (hNT) [Pleasure et al., 1993]. Briefly, the NT2 (NTera2/D1) cell line represents a committed neuronal precursor stage of differentiation. The NT2 cells are induced by retinoic acid (RA) to differentiate in vitro into postmitotic central nervous system neurons (hNT). In the course of the differentiation process, the NT2 cells lose neuroepithelial markers and gain markers specific for mature neurons. The hNT neurons are produced by culturing of NT2 cells in DMEM supplemented with glutamine and 10% (v/v) FBS. The cells are grown for five weeks in the presence of RA and then harvested by mild trypsinization. The cells are replated and allowed to grow for several days wherein 10–20% have begun to differentiate into postmitotic neurons (hNT). Mitotic inhibitors are added to the medium to prevent overgrowth by undifferentiated cells and after ten day the hNT cells are harvested and used immediately or cryopreserved for later use.

During the process of maturation (differentiation) the NT2 cells loose neuroepithelial markers and gain those specific for mature neurons. After transplantation into athymic (nude) mice, hNT neurons can integrate and change phenotype into neurons similar to the target neurons and survive >14 months. [Kleppner et al., 1995]. These results suggests the usefulness of hNT neurons for screening the effects of trophic factors, similar to those lacking in the target area, thus providing evidence that Sertoli cells can provide such support.

Cryopreserved hNT neurons were thawed rapidly at 37° C. and transferred into DMEM-F12+10% Fetal bovine serum (FBS) in a 15 cc centrifuge tube. The cells were then centrifuged at 800 rpm for five minutes. The supernatant was discarded and the cells resuspended in DMEM+1% FBS in 48 well plates. The post-thaw viability was assessed by trypan Blue dye exclusion method prior to seeding at a density of 1×10$^5$ cells/cm$^2$. After 24 hours, the medium was changed to serum-free DMEM:F12 supplemented with gentamicin, ITS, and retinol.

The dose response study was performed by adding thawed cryopreserved porcine Sertoli cells to the hNT neurons in the wells at the following ratios (SC:hNT): 0:1, 1:1, 2.5:1, 5:1. The control for the dose-response was no Sertoli cells.

Immunocytochemistry and quantification of cell numbers, soma size, neurite outgrowth and number of branching points: Immunocytochemistry was performed using a monoclonal primary antibody against TH (1:2000, Incstar) and as a secondary antibody, biotinylated horse anti-mouse (1:300, Vector, Burlingame, Calif., USA). The antibody complex was developed using avidin-biotin complex (ABC-elite kit; Vector) (Diaminobenztropine (DAB-kit, Vector) was used to visualize the developed product.

The survival or induction of TH-positive neurons was assessed at ×200 magnification in a blind coded manor using a 400 μm ocular grid to cover almost 2% of the total area when placed in 10 placements for each well. The morphological evaluation was conducted at a co-culture ratio of 1:1, and 50 cells from 5 independent cultures were evaluated by measurement with the above mentioned reticule grid at ×200 magnification.

Isolation and Pretreatment of Sertoli Cells and Peritubular Cells: As previously described (Cameron and Muffly, 1991) decapsulated rat or other mammalian testes were subjected to sequential enzymatic treatment at 37° C. using 0.25% trypsin (Sigma) and 0.1% collagenase (Sigma, type V) (Cameron et al. 1987a; Cameron et al. 1987b). The resulting Sertoli cell aggregates were equally distributed in a volume of 20ml incubation medium into 75 cm$^2$ tissue culture flasks (Costar). The Sertoli cells after the last step of the isolation were plated at a density of 5×10$^6$ cells/T-75 flasks (Corning) in DMEM:F12 (Life Technologies)+1% FBS supplemented with ITS (Collaborative research), retinol (Sigma), and gentamicin (Sigma). Plated Sertoli aggregates were incubated at 39° C. in 5% $CO_2$–95% air for 48 hours which preferentially selects for Sertoli cells over germ cells. After this incubation cells were subjected to hypotonic treatment with sterile 0.5 mM Tris-HCl buffer for one minute (Galdieri et al. 1981) to expedite the removal of contaminating germ cells. Following two washes with incubation medium, flasks were replenished with 20 ml incubation medium and returned to the $CO_2$-injected incubator at 37° C. in 5% $CO_2$–95% air. The resulting pre-treated Sertoli-enriched monocultures contained greater than 95% Sertoli cells. Plating density of <2.0×10$^6$ Sertoli cells/cm$^2$ generally did not result in a confluent monolayer of cells. For cryopreservation of the Sertoli cells after 48 hours in culture the cells were frozen in DMEM:F12+10% DMSO +10% FBS. Alternatively the cells were washed two times to be used fresh as indicated.

Incubation Medium and Sertoli Cell Conditioned Medium:

The incubation (control) medium used for Sertoli cell culture and co-culture was Dulbecco's Minimum Essential Medium:Ham's F12 Nutrient Medium (Whittaker Bioproducts) mixed 1:1 and supplemented with 3 mg/ml L-glutamine (Sigma, grade III), 0.01 cc/ml insulin-transferrin-selenium (ITS, Collaborative Research, Inc.), 50 ng/ml retinol (Sigma), 19 μl/ml lactic acid (Sigma) and 0.01 cc/ml gentamicin sulfate (Gibco).

Following the first 48 hour incubation period of isolated Sertoli cells (rat or porcine as indicated in text), conditioned media was collected and centrifuged at 1500 rpm for five minutes. The supernatant was collected and immediately frozen in sterile test tubes. This medium was identified as Sertoli conditioned medium (SCM).

Example 1

Enhanced Viability of Cryopreserved Cells and Post-Thaw Viability with Sertoli Cells and Sertoli Cell Conditioned Medium (SCM):

Cell transplantation therapies are optimized by the availability of cryopreserved cells which have high post-thaw viability. Fetal brain cells are not cryopreserved well. To enhance the post-thaw recoverability and viability of fetal brain cells (FBC), the cryoprotectant properties of Sertoli cells and Sertoli cell pre-conditioned medium (SCM) on rat fetal brain cells (FBC) including ventral mesencephalon, commercially available immature brain cells (hNT) and striated lateral and medial eminence cells were investigated.

Fetal brain cells (FBC) were collected from the ventral mesencephalon of fetal rats (15–17 days gestation). The fetal brain tissue was suspended in medium and initially dispersed by passing it through a series of sequentially decreasing sized hypodermic needles (18–26 gauge). The resulting suspension was treated with 0.1% trypsin for five minutes and followed by 0.1% trypsin inhibitor for two minutes. The suspended FBC were washed (3x), resuspended in incubation medium and plated in poly-L-lysine-coated culture vessels. The hNT cells are derived from NT2 cells (STRATAGENE).

Studies utilizing rat Sertoli Cells:

hNT cells or cells from the ventral mesencephalon (VM) of embryonic E15 rats were isolated and either cryopreserved alone, with rat Sertoli cells (SC) (FIG. 1A) or incubated in rat SCM after thawing and post-thaw viability determined. Cryopreservation with Sertoli Cells significantly increased post-thaw viability of FBS (FIG. 1A) and hNT. Additionally, it was determined that incubation in SCM after thawing increased post-thaw viability.

Monocultures of FBC and hNT cells (approximately $5 \times 10^6$/ml) were cryopreserved at high density in SCM+10% DMSO or control medium+10% DMSO and stored in liquid nitrogen. Quickly thawed cells were washed and resuspended in warm SCM. Samples were collected for cell number and live/dead percent estimations by duplicate, blind counts by three separate individuals.

The percent of post-thaw live cells, estimated by vital dye exclusion, doubled for FBC and hNT cells cryopreserved in SCM when compared to cells cryopreserved in control medium. The mean post-thaw hNT cells recovered from SCM medium ($2.0 \times 10^6$/ml) was significantly ($P<0.05$) greater than the mean post-thaw hNT recovered from control medium ($1.4 \times 10^6$/ml).

| PERCENT INCREASE OF VIABILITY OVER CONTROLS | |
| --- | --- |
| FBC + SCM | 10% |
| hNT + SCM | 43% |

The results show that media soluble factors secreted by Sertoli cells enhanced the post-thaw viability of FBC, and hNT cells.

Figure 1B:
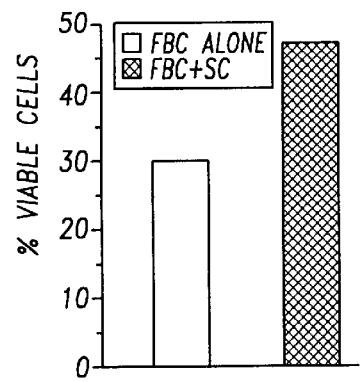
Figure 1C:
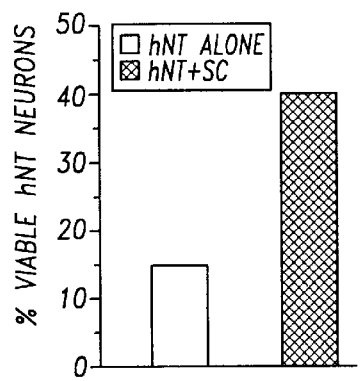

Studies Utilizing Porcine Sertoli Cells:

FIGS. 1B and 1C demonstrate that rat FBC and hNT cells, respectively, when co-cryopreserved (as described herein above) with porcine Sertoli cells have enhanced post-thaw viability.

Figure 1D:
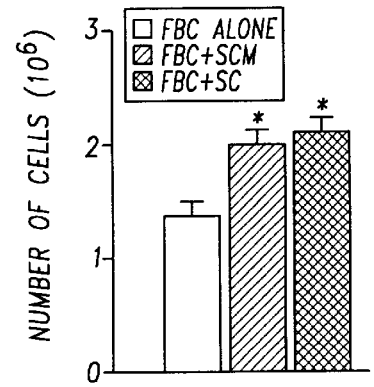

The number of rat FBC recovered following cryopreservation (FIG. 1D) was significantly increased ($p<0.05$) when the cells were cryopreserved with porcine Sertoli cells (Mean±SEM: $2 \times 10^6$/ml ±$0.2 \times 10^6$/ml) or cryopreserved in porcine SCM ($2 \times 10^6$/ml ±$0.2 \times 10^6$/ml) when compared to FBC cells cryopreserved in control medium only ($1.4 \times 10^6$/ml ±$0.2 \times 10^6$/ml). The percent of post-thaw viable cells, estimated by vital dye exclusion was significantly increased ($p<0.05$) for FBC cryopreserved with Sertoli Cells when compared to FBC cryopreserved without Sertoli Cells.

Figure 1E:
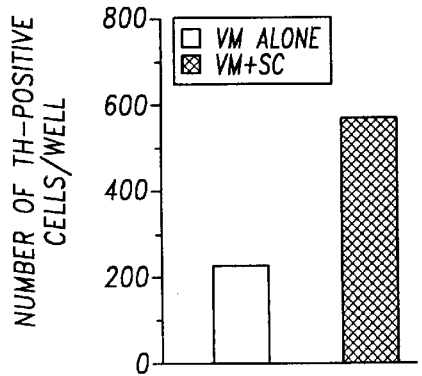

Cryopreserved VM cells were thawed and incubated with or without Sertoli cells for 24 hours. The presence of Sertoli Cells in the post-thaw co-culture (SC:VM:1:1) significantly ($p<0.05$) increased the number of TH-immunopositive VM cells (592±177) when compared to past-thaw VM cell monoculture (224±77) plated at the same density (FIG. 1E).

Example 2

Figure 2A:
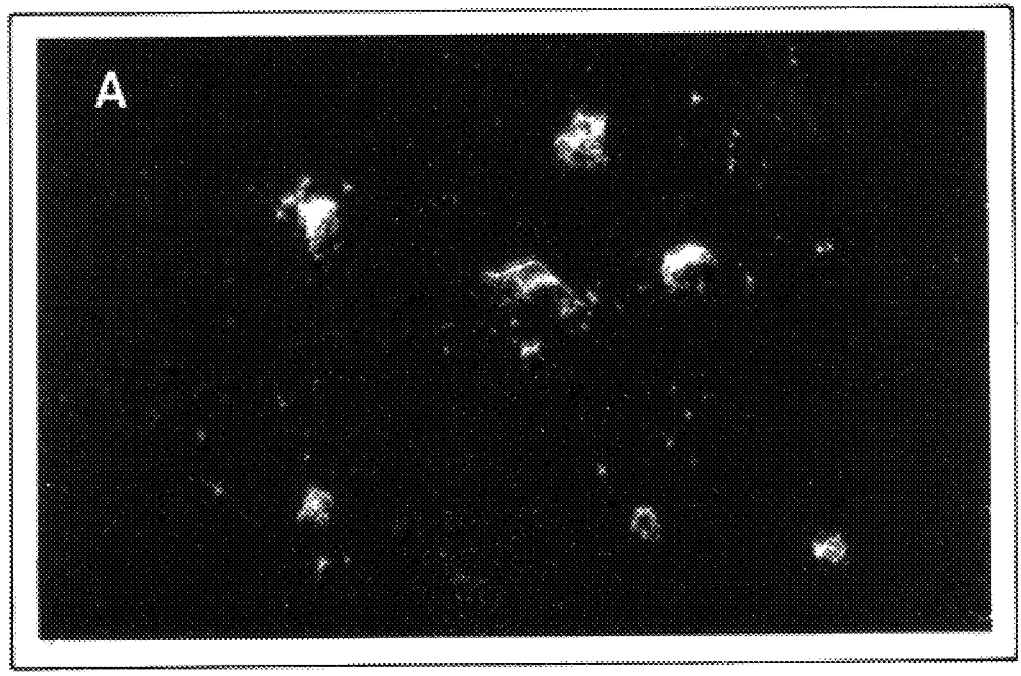
FIGS. 2A–C are light interference micrographs illustrating cells from the ventral mesencephalon of fetal rats (VM) isolated and cultured for seven days in control medium (CM) or Sertoli cell pre-conditioned medium (SCM) and photographed with darkfield, interference contrast optics, wherein (A) depicts VM cells incubated in CM showing no evidence of stimulation or differentiation,(B) depicts VM cells incubated in SCM appearing highly stimulated, and (C) at higher magnification, depicts VM cells incubated in SCM exhibiting neurite outgrowth.
Figure 2B:
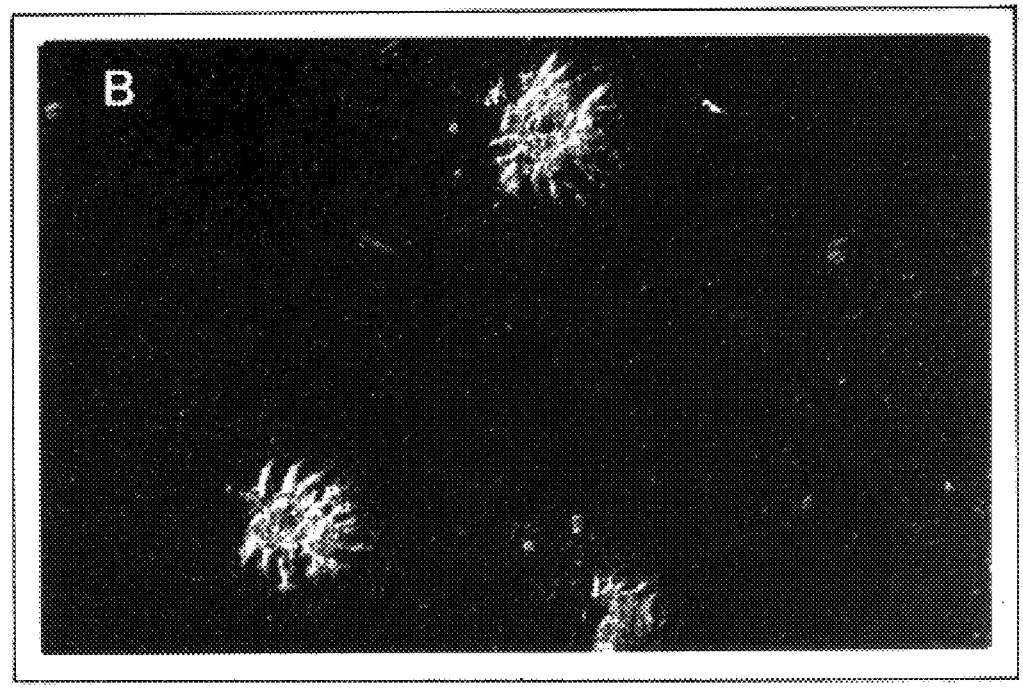
Figure 2C:
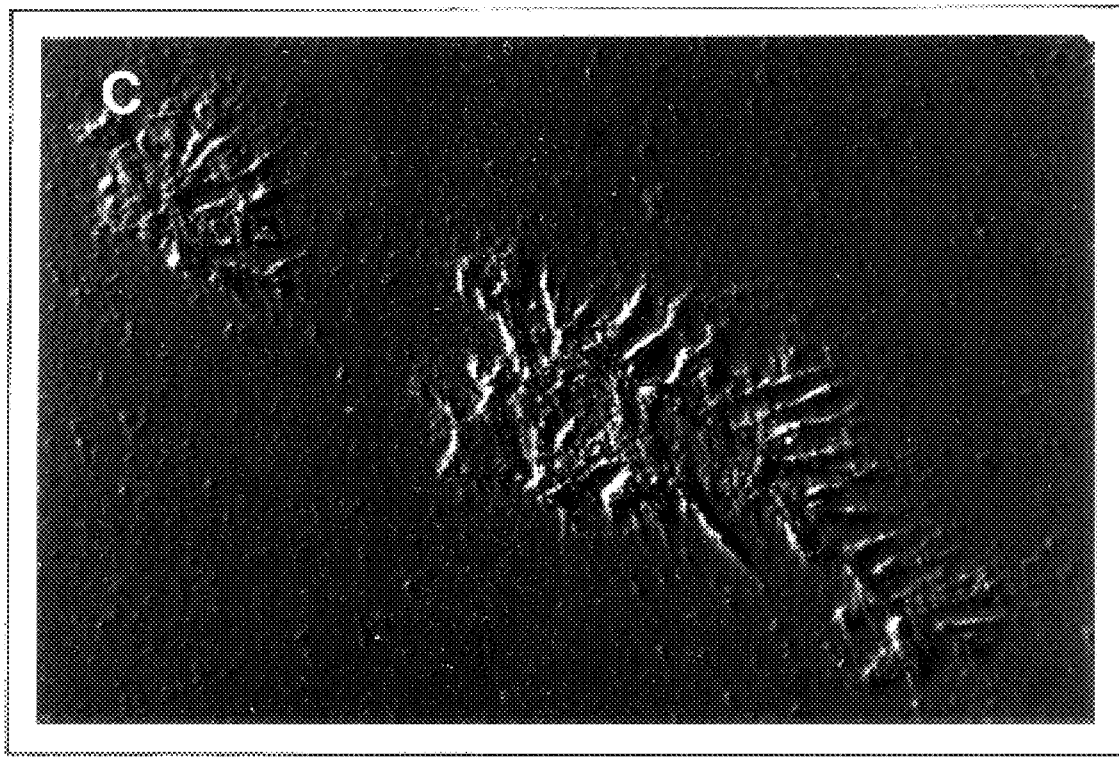
Figure 3A:
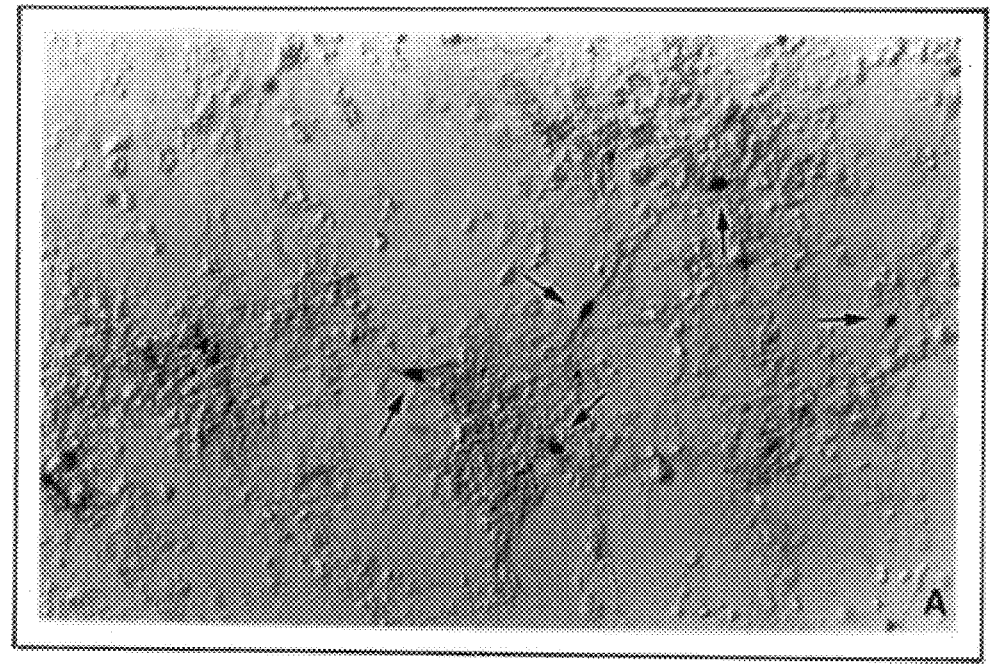
FIGS. 3A–B are photomicrographs of tyrosine-hydroxylase (TH) immunostained cultures in (A) control cultures and (B) rat Sertoli-cell conditioned media treated cultures at 7 days in vitro, wherein arrows indicate TH-positive cells, magnification ×100.
Figure 3B:
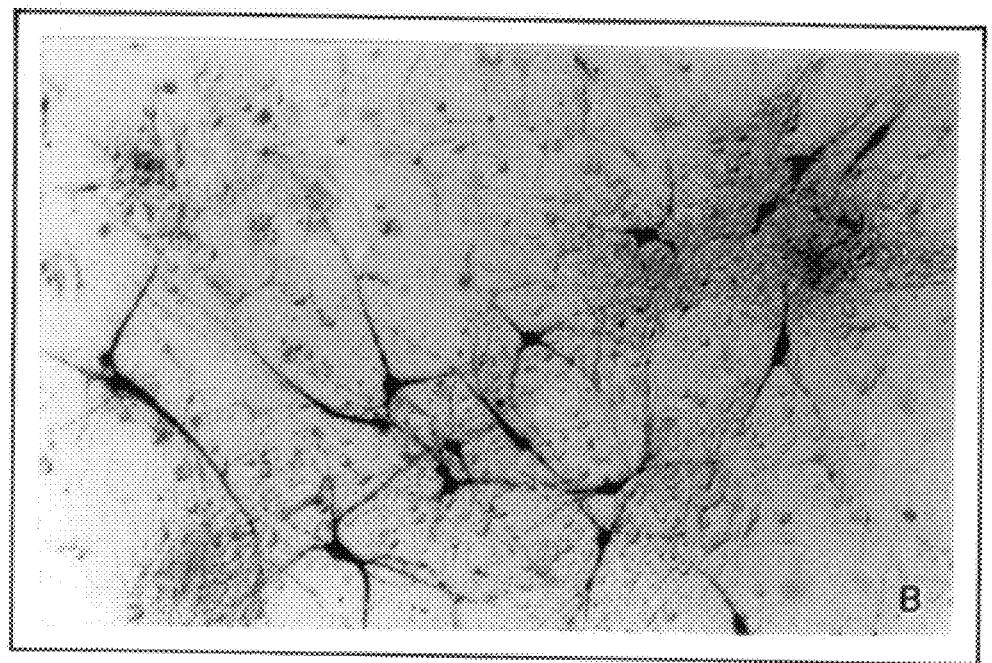

The effect of rat Sertoli Cell Conditioned Media on rat VM cells:

To provide evidence for secretion and release of trophic factors by Sertoli Cells, fetal dopaminergic neurons were cultured in Sertoli Cell conditioned medium (SCM). As described herein above, fetal ventral mesencephalon cells were obtained from E15 rats and were cultured for seven days with or without rat SCM (FIGS. 2–3). Referring to FIG. 2B, VM cells incubated in SCM were highly stimulated as compared to the control (FIG. 2A). FIG. 2C illustrates that at higher magnification, VM cells incubated in SCM show neurite outgrowth.

Figure 4:
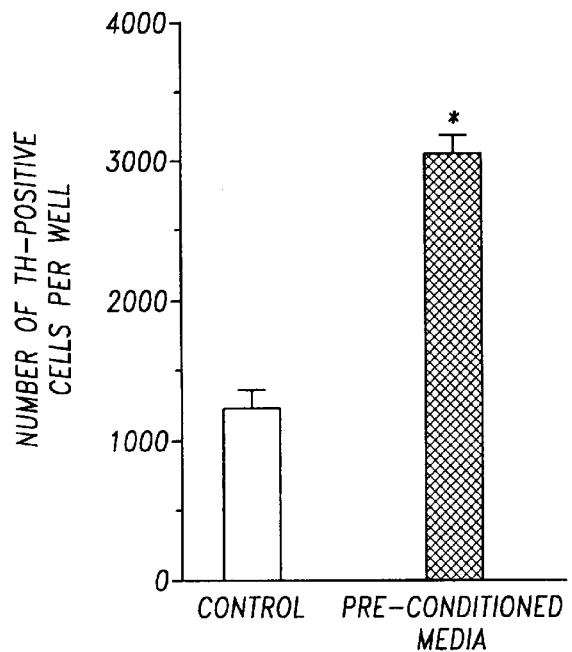
FIG. 4 is a bar graph showing the effect of rat Sertoli conditioned media on the yield of tyrosine hydroxylase (TH)-positive neurons as 7 days in vitro wherein data represents the mean ±S.E.M. of four independent culture experiments, * denotes, p<0.028, significant difference from control.

After 7 days in culture, the cells were fixed with 4% formaldehyde and stained for Tyrosine Hydroxylase (TH) immunoreactivity (FIG. 3). The number of TH-positive cells showed a significant increase ($p<0.028$) over the control in these culture conditions (FIG. 4).

Example 3

Figure 5A:
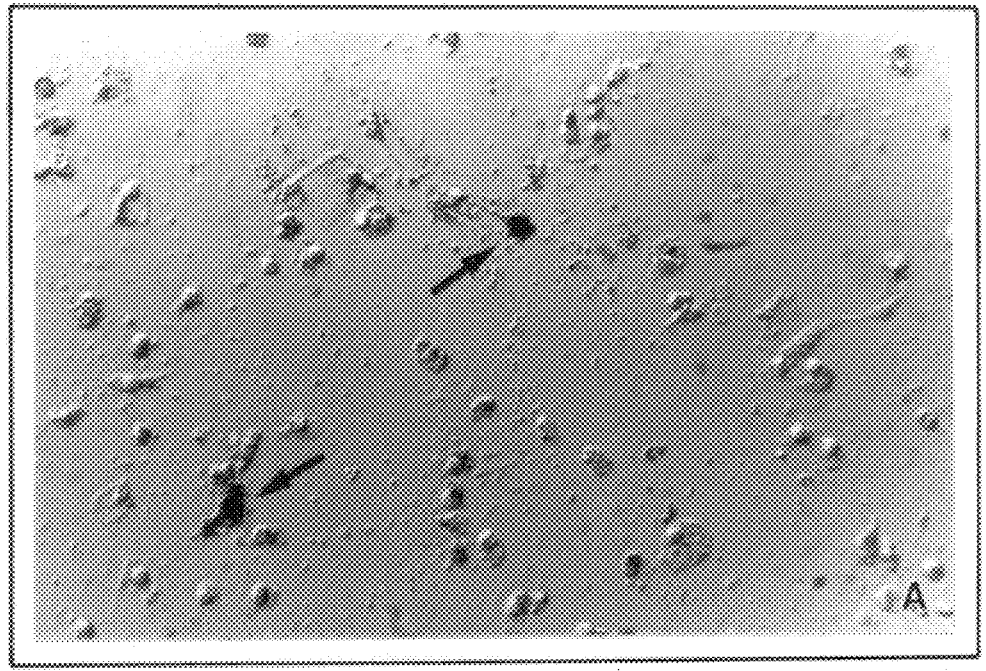
FIGS. 5A–B are photomicrographs of tyrosine-hydroxylase (TH) immunostained (A) E15 ventral mesencephalic cultures alone and (B) porcine Sertoli-cell co-cultures at 7 days in vitro, arrows indicate TH-positive cells, magnification ×200.
Figure 5B:
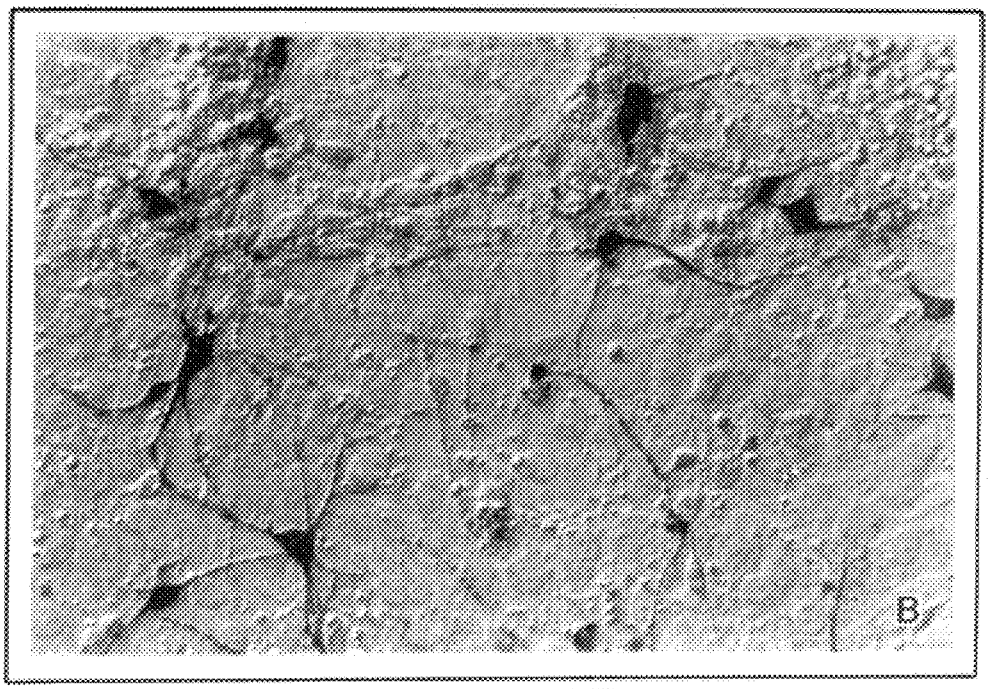

The effect of Sertoli cells on rat embryonic DA neurons:

To determine the survival and trophic effect of porcine Sertoli cells on rat embryonic mesencephalic DA neurons, Applicants co-cultured fresh or thawed cryopreserved primary porcine Sertoli cells and E15 mesencephalic neurons in supplemented media on poly-L-lysin coated 48 well tissue culture plates. After 7 days in culture, the cells were fixed with 4% formaldehyde and stained for Tyrosine Hydroxylase (TH) immunoreactivity (FIG. 5).

Figure 6A:
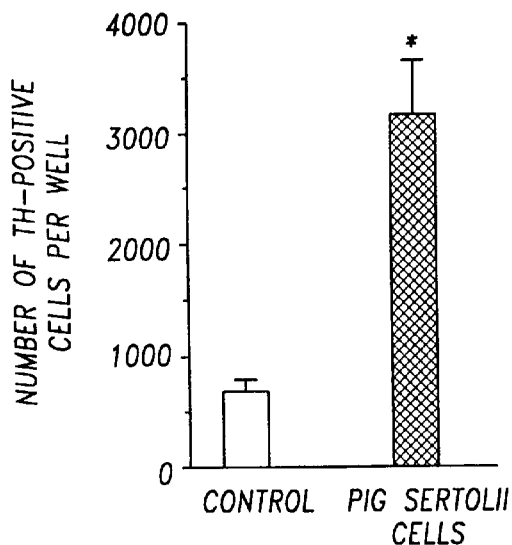
FIGS. 6A–D are bar graphs showing the effect of co-culture with porcine Sertoli cells on the yield of rat (E15) fetal mesencephalic TH-positive neurons at (A) 7 day in vitro, (B) size of soma area, (C) length of the longest primary neurite, and (D) number of primary neurites per cell wherein data represents the mean ±S.E.M. of four independent culture experiments, * denotes, p<0.0001, significant difference from control.
Figure 6B:
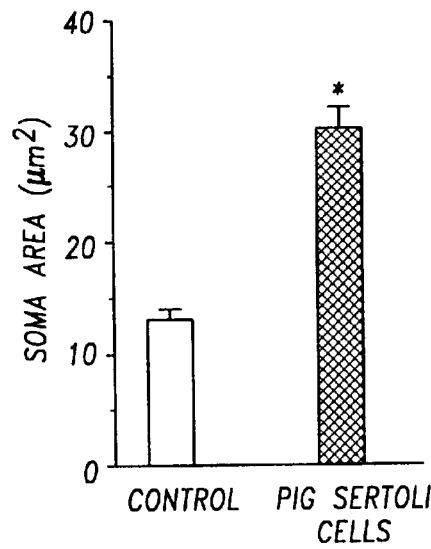
Figure 6C:
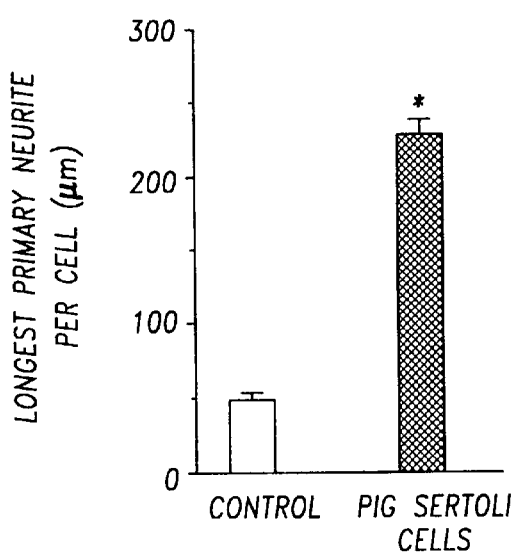
Figure 6D:
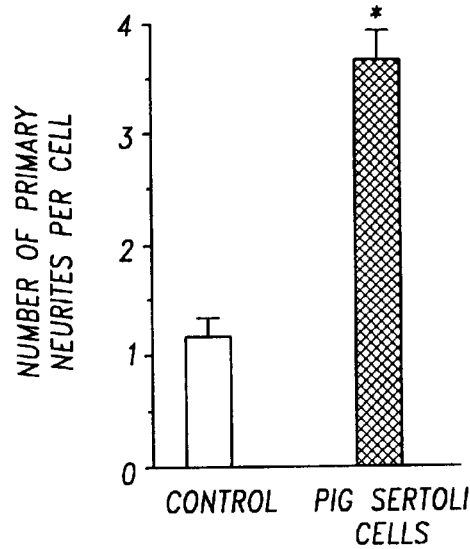

The trophic effect was assessed by measuring soma size, neuritic outgrowth, and number of branching points in a culture with Sertoli:VM ratio of 1:1 (FIG. 6A–D). The TH number was estimated in the culture and showed an significant increase in TH-positive neurons with 3198+478 in the treated group compared to control 712+121 ($p=0.028$) (FIG. 6A). The Sertoli co-cultured TH-positive cells showed a significant 2.4-fold increased soma size 31.85±2.23 $\mu$m ($p<0.005$) compared to control 13.23±1.01 $\mu$m, (FIG. 6B). The increase in length (228±13 $\mu$m) of the longest neurite differed significantly, ($p<0.0001$) in the treated group (FIG. 6C), when compared to the control (49±3 $\mu$m), which represents a 4.6-fold increased sprouting of the longest neurite per cell. The number of branching points was increased from 1.12±0.166 in the control to 3.74±0.183 in the Sertoli co-cultured DA-neurons (FIG. 6D).

Figure 7:
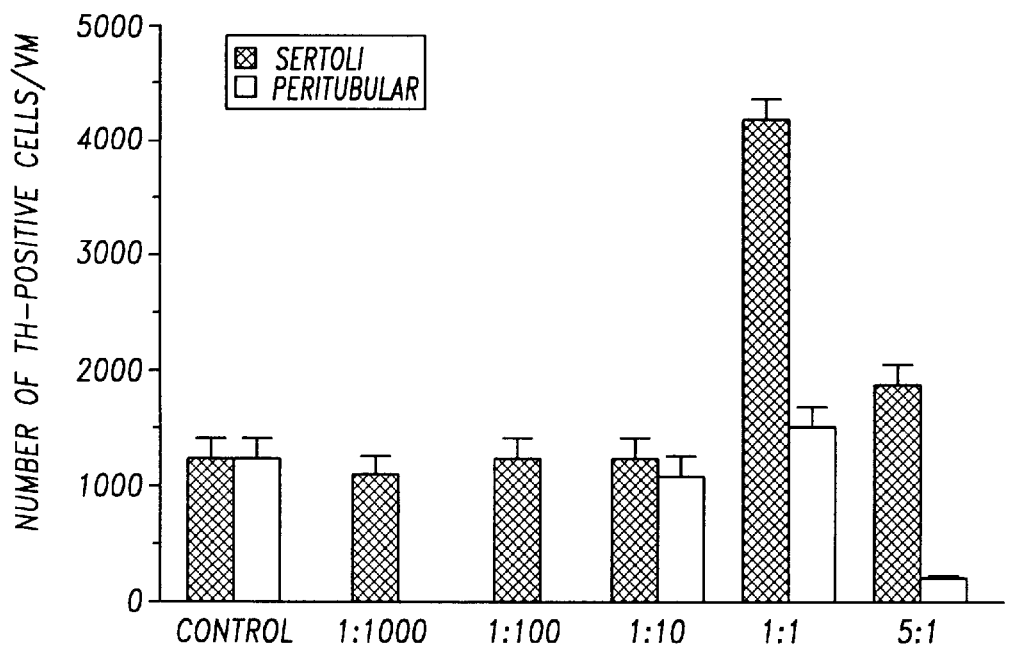
FIG. 7 is a bar graph showing the effects of porcine Sertoli and Peritubular cells on rat E15 ventral mesencephalic cultures.

To determine the effect of freshly isolated porcine Sertoli cells and to exclude an effect generated by contaminating cells, Applicants conducted a study with fresh porcine Sertoli and Peritubular cells, consisting of five different ratios (1:1000, 1:100, 1:10, 1:1 and 5:1) (FIG. 7). The 1:1 ratio of Sertoli:VM cells showed a significant 3.2-fold increase in the number of TH-positive neurons (4183±177) compared to control (1297±127). No effect was seen with peritubular cells on increase of TH-positive neurons at any of the ratios. However a significant decrease ($p=0.003$) in the number of TH-positive cells (132±34) was seen at the 5:1 ratio of Peritubular:VM compared to control.

Figure 8:
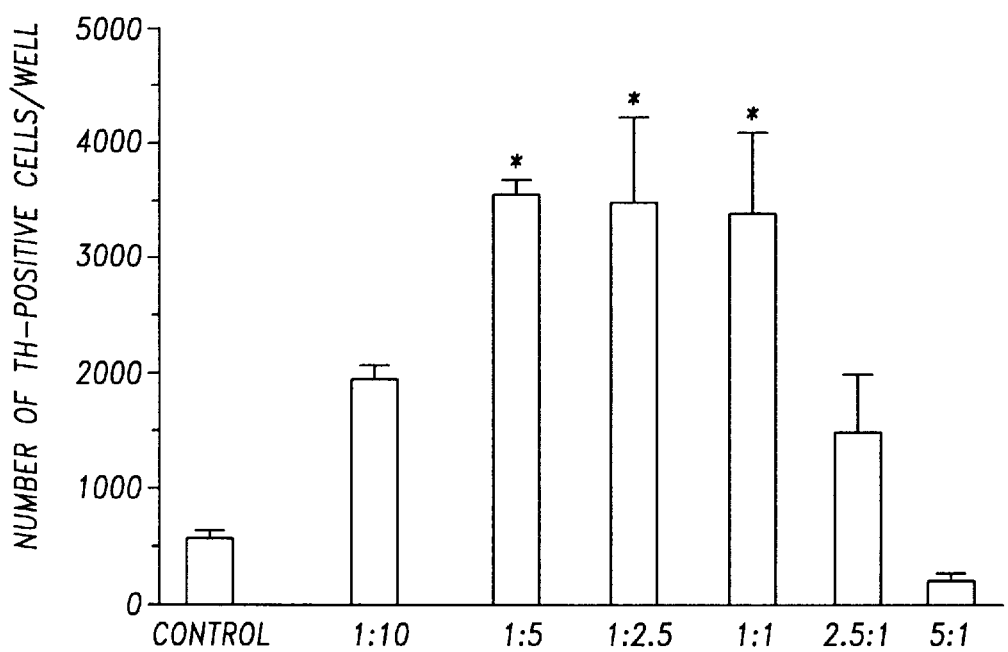
FIG. 8 is a bar graph showing the effect of previously cryopreserved Sertoli cells on rat E15 ventral mesencephalic DA neurons.

To determine if the survival and trophic effect of cryopreserved porcine Sertoli cells would generate the same results as freshly isolated Sertoli Applicants performed a dose-response study with six different ratios of cryopreserved Sertoli cells and E15 VM neurons (1:100, 1:10, 1:2.5, 1:1, 2.5:1, and 5:1) (FIG. 8). Maximal responses were seen at SC:VM ratios of 1:5, 1:2.5 and 1:1, with the ratio 1:5 showing 3570±139 TH-positive cells, and the 1:1 ratio resulting in 3437±740, which is a 5.6-fold significant increase ($p=0.0012$), compared to control with 612±72 cells. The ratio 5:1 had a significantly decreased number of TH-positive cells, 224±102, compared to the ratios 1:5–1:1 ($p=0.0014$).

Figure 9:
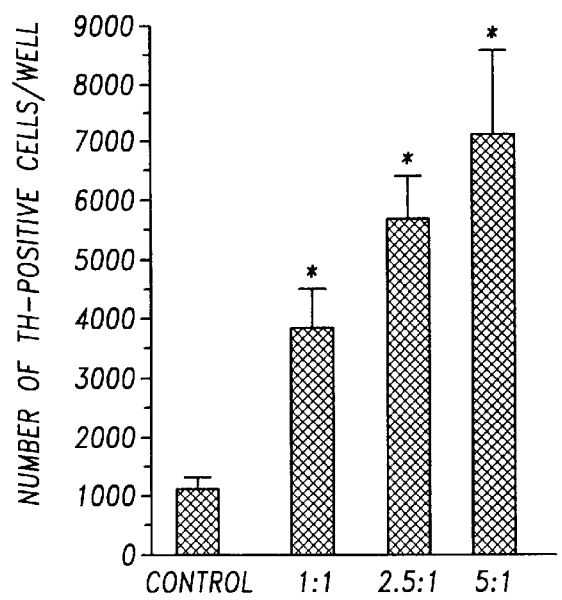
FIG. 9 is a bar graph showing the effect of porcine Sertoli cells co-culture on absolute number of DA neurons from hNT neuron culture.

Example 4
The effect of Sertoli cells on VM and hNT cells in culture:

To investigate whether porcine Sertoli cells had an effect on the induction of Tyrosine Hydroxylase (TH) of cryopreserved hNT neurons and/or induction of phenotypic appearance, Applicants conducted a dose-response study with three different concentrations; 1:1, 2.5:1, and 5:1 (Sertoli cells:hNT). The results showed an increase in number of TH-positive neurons and a morphological change in maturation. The number of TH-positive cells, was significantly increased for all ratios. The most pronounced effect, a nearly sixfold increase ($p<0.0001$), was found in the co-cultures with a ratio of 5:1 Sertoli cells:hNT neurons, in which 7262±1348 TH-positive neurons survived for 7 days in vitro compared to 1215±203 in the control (FIG. 9). The mean post-thaw viability was 65% of the hNT neurons.

Figure 10A:
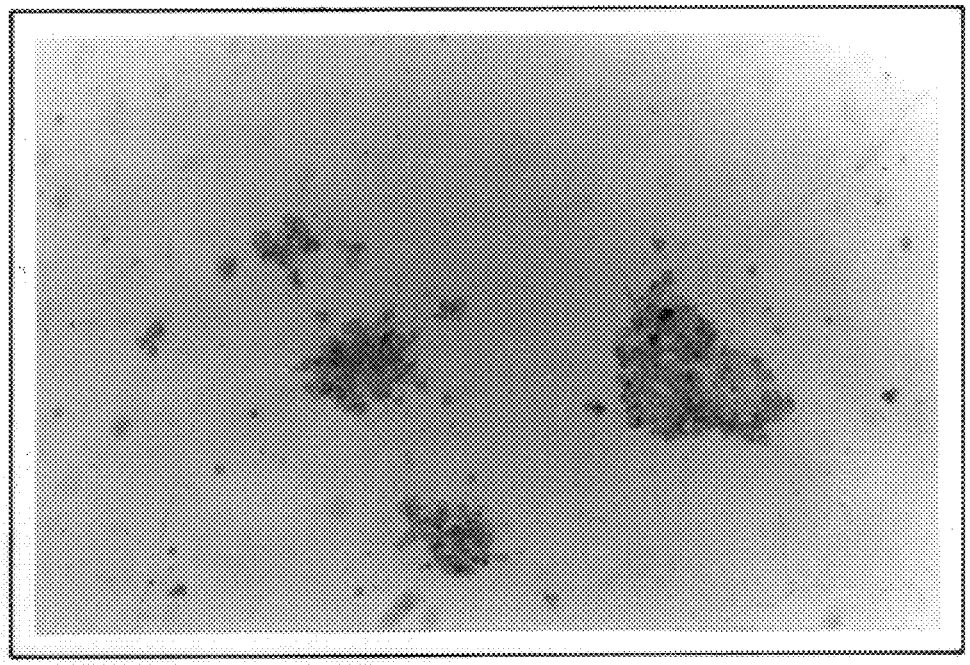
FIGS. 10A–B are photomicrographs of tyrosine hydroxylase (TH)-positive hNT neurons in (A) control and in co-culture with (B) porcine Sertoli cells isolated from 2.5 month old animals, note extended neurite outgrowth in (B), arrow TH-positive neuron, magnification ×100.
Figure 10B:
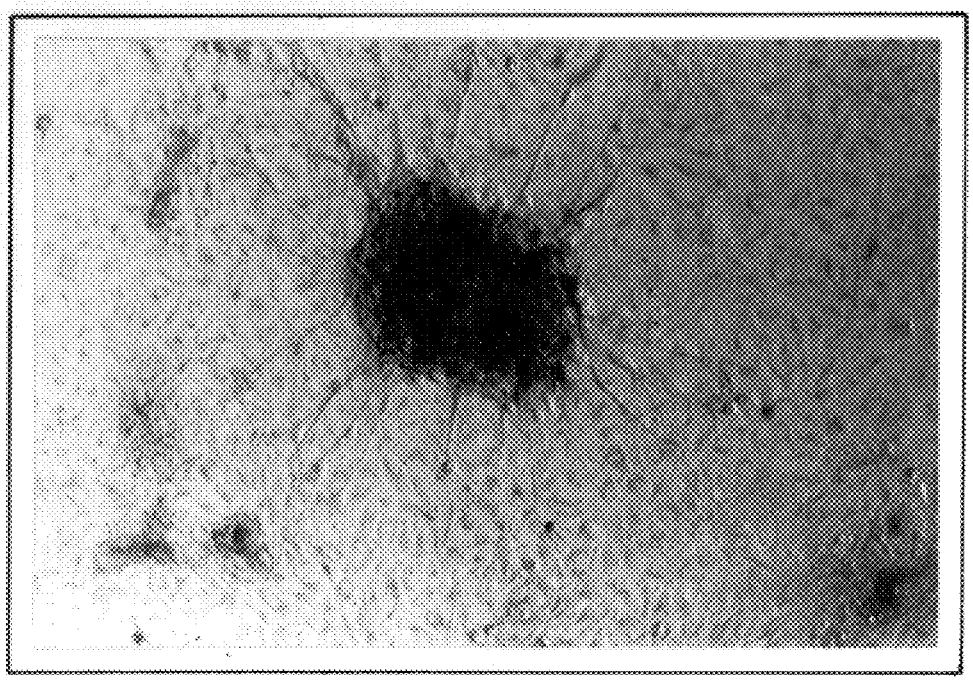

In the control cultures, the cells tended to stay in clusters (FIG. 10A), but when co-cultured with Sertoli cells the hNT cells were migrating and also extended longer neuritic processes (FIG. 10B) as assessed morphologically in a phase contrast microscope.

Example 5

Survival of Sertoli Cells in the Brain

Sertoli cell/chromaffin cell co-grafts were transplanted into the striatum of the brain (Sanberg et al, 1996). Transplanted chromaffin cells were present and easily identified because of the inclusion of secretory granules unique to the cells. Co-transplanted Sertoli cells were detected immediately adjacent to the electron dense chromaffin cells. This demonstrates the survival of co-grafted adrenal chromaffin cells with Sertoli cells in the brain.

Example 6
Effects of Cyclosporine A (CsA) on the survival of transplanted Sertoli cells:

Fluorescent cell labeling: Immediately prior to transplantation (approximately two hours), Sertoli cell monocultures prepared as described herein were treated with CM-DiI fluorescent dye for cell tracking (100(1 stock/ml medium; Molecular Probes, Inc., Eugene, Oreg.) for seven minutes at 37° C. and then placed in the refrigerator (4° C.) for an additional 15 minutes. Fluorescent "tagged" Sertoli cells were washed (three times) and resuspended in 1 ml of incubation medium.

The effect of cyclosporine A on the survival of grafted Sertoli cells in situ was examined. Grafted Sertoli cells were labeled with a fluorescent tag (DiI) prior to transplantation into the striatum of the brain. The tissue was collected one month post-transplantation. Viable fluorescent Sertoli cells were seen in a rat host that had not received immunosuppression therapy with cyclosporine A. Viable fluorescent Sertoli cells are found in a rat host that did receive cyclosporine A immunosuppression therapy. This example demonstrates that cyclosporine A is not necessary for the survival of Sertoli cells transplanted into the brain.

Throughout this application, various publications, including United States patents, are referenced by citation or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

| Category and Protein | Function |
| --- | --- |
| Hormones/Growth Factors | |
| Mullerian Inhibiting Substance | inhibits Mullerian duct |
| Inhibin | inhibits FSH release |
| Insulin-like Growth Factor | |
| (Sommatomedins A and C, IGF) | growth factor |
| Prodynorphin | |
| Interleukin-1α | mitogen |
| Transforming Growth Factor α & β | growth factors |
| Basic Fibroblast Growth Factor | growth factor |
| LHRH-like Factor | Leydig cell steroidogenesis |
| Sertoli Secreted Growth Factor | growth factor |
| Seminiferous Growth Factor | |
| Leydig Cell Stimulatory Activity | |
| Testins | |
| CMB proteins | |
| Vitamin Binding Proteins | vitamin transport |
| Transport and Bioprotection | |
| Transferrin | iron transport |
| Ceruloplasm | copper transport |
| Saposin SGP-1 | binds glycosphinogolipids |
| SGP-2 (Clusterin) | lipid transport |
| Androgen Binding Protein | transports T and DHT |
| SPARC | calcium binding protein |
| IGF Binding Proteins | IGF transport |
| Riboflavin Binding Protein | riboflavin transport |
| Proteases and Protease Inhibitors | |
| Plasminogen Activator | protease |
| Cyclic Protein-2 | protease inhibitor |
| Cystatin | protease inhibitor |
| α$_2$-Macroglobulin | protease inhibitor |
| Type IV Collagenase | protease |
| Metalloproteinases | protease |
| Basement membrane | |
| Collagen IV | |
| Laminin | |
| Proteoglycans | |
| Immunoprotective Factors | |
| Fas-L | |
| Activin | |

REFERENCES

Beck et al., (1993). The nature of the trophic action of brain-derived trophic factor, des(1–3)-insulin like growth factor-1, and basic fibroblast growth factor on mesencephalic dopaminergic neurons developing in culture. *Neurosci.*, 52:855–866.

Bellgrau (1995). A role for CD95 ligand in preventing graft rejection. *Nature*, 377:630–632.

Berden et al., (1985). Severe central nervous system toxicity associated with cyclosporine *Lance* 26:219–220.

Bitgood et al., (1996). Sertoli cell signaling by Desert hedgehog regulates the male germline. *Curr. Biol.*, 6:298–304.

Bjorklund and Stenevi, (1985). Intracerebral neural grafting: a historical perspective. in Bjorklund, A. and U. Stenevi, eds. *Neural grafting in the mammalian CNS*, Amsterdam: Elsevier, 3–11.

Bjorklund, (1992). Dopaminergic transplants in experimental Parkinsonism: Cellular mechanisms of graft-induced functional recovery. *Current Biology*, 2:683–689.

Borlongan et al., (1995). Cyclosporine-A increases spontaneous and dopamine agonist-induced locomotor behavior in normal rats. *Cell Transplant.*, 4:65–73.

Borlongan et al. (1995). Systemic 3-nitropropionic acid: Behavioral deficits and striatal damage in rats. *Brain Research Bulletin*, 36:549–556.

Borlongan et al., (1997). Intracerebral transplantation of testis-derived Sertoli cells in female rats with 6-hydroxydopamine-induced parkinsonism promotes functional recovery. *Exp. Neurol.*, in press, 1997.

Bowenkamp et al., (1995). Glial cell line-derived neurotrophic factor supports survival of injured midbrain DA neurons. *J. Comp. Neurol.*, 355:479–489.

Cameron et al., (1990). Successful islet/abdominal testis transplantation does not require Leydig cells. *Transplantation*, 50:649–653.

Cameron and Muffly, (1991). Hormonal regulation of spermated binding to Sertoli cells in vitro *J. Cell Sci.*, 100:532–533.

Carson et al., (1984). Synthesis and secretion of a novel binding protein for retinol by a cell line derived from Sertoli cells. *J. Biological Chemistry*, 269:3117–3123.

Chen et al., (1996). The effect of prior in vitro exposure of donor cells to trophic factors in neuro transplantation. *Exp. Neurol.*, 138:64–72.

Choi-Lundberg and Bohn, (1995). Ontogeny and distribution of glial cell line derived neurotrophic factor (GDNF) mRNA in rat. *Develop. Brain Res.*, 85:80–88.

Collard et al., (1988). Biosynthesis and molecular cloning of sulfated glycoprotein-1 secreted by rat Sertoli cells: sequence similarities with the 70-kilodalton precursors to sulfatide/GM1 activator. *Biochemistry*, 27:4557–4560.

de Groen et al., (1984). Central nervous system toxicity after liver transplantation. *N. Engl. J. Med.*, 14:861–866.

Dunnett and Bjorklund, (1994). in *Functional Neural Transplantation, Advances in Neuroscience*, Volume 2, Raven Press, New York.

Engele and Bohn, (1991). The neurotrophic effects of fibroblast growth factor on dopaminergic neurons in vitro are mediated by mesencephalic glia. *J. Neurosci.*, 11:3070–3078 (1991).

Freeman et al., (1994). The USF protocol for fetal nigral transplantation in Parkinson's disease *Experimental Neurology*, 129:6–7.

Freeman et al., (1995). Bilateral fetal nigral transplantation into the postcommissural putamen in Parkinson's disease. *Ann. Neurol.*, 38:379–388.

Gash et al., (1996). Functional recovery in parkinsonian monkeys treated with GDNF. *Nature*, 380:252–255.

Griswold, (1992). Protein secretion by Sertoli cells: general considerations in Russel, L. D. and M. D. Griswold, eds. *The Sertoli Cell*, Cache River Press, Clearwater, Fla., 195–200.

Hedges (1989). The testis: an immunologically suppressed tissue? *Reprod. Fertil Dev.*, 1:75.

Hiraiawa et al., (1992). Binding and transport of gangliosides by prosaposin. *Proc. Natl. Acad. Sci. USA*, 89:11254–11258.

Hudson et al., (1995). Glial cell line-derived neurotrophic factor augments midbrain dopaminergic circuits in vivo. *Brain Res. Bull.*, 36:425–432.

Hyman et al., (1991). BDNF is a neurotrophic factor for dopaminergic neurons of the substantia nigra. *Nature*, 350:230–232.

Hynes et al., (1995). Control of neuronal diversity by the floor plate, contact-mediated induction of mid-brain DA neurons. *Cell*, 80:95–107.

Igdoura et al., (1996). Trafficking of sulfated glycoprotein-1 (prosaposin) to lysosomes or to the extracellular space in rat Sertoli cells. *Cell Tissue Res.*, 283:385–394.

Isacson et al., (1986). Graft-induced behavioral recovery in an animal model of Huntington's disease. *Proc. Natl. Acad. Sci.*, 83:2728–2732.

Kleppner et al., (1995). Transplanted human neurons derived from a teratocarinoma cell line (Ntera-2) mature, integrate and survive for over 1 year in the nude mouse brain. *J. Com. Neurol.*, 357:618–632.

Knusel et al., (1990). Selective and nonselective stimulation of central cholinergic and dopaminergic development in vitro by nerve growth factor, basic fibroblast growth factor, epidermal growth factor, insulin and the insulin-like growth factors I and II. *J. Neurosci.*, 10:558–567.

Knusel et al., (1991). Promotion of cholinergic and dopaminergic neuron differentiation by brain-derived neurotrophic factor but not neurotrophin-3. *Proc. Natl. Acad. Sci. USA*, 88:961–965.

Kondoh et al., (1993). Distribution of prosaposin-like immunoreactivity in rat brain. *J. Comp. Neurol.*, 334:590–602.

Kordower et al., (1995). Neuropathological evidence of graft survival and striatal reinnervation after the transplantation of embryonic mesencephalic tissue in a patient with Parkinson's disease. *New Engl. J. Med.*, 332:1118–1124.

Kordower et al., (1996). Functional embryonic nigral grafts in a patient with Parkinson's disease, Chemaonaotimic, ultrastructural and metabolic studies. *J. Comp. Neurol.*, 370:203–230.

Kotani et al., (1996). A hydrophilic peptide comprising 18 amino acid residues of the prosaposin sequence has neurotrophic activity in vitro and in vivo. *J. Neurochem.*, 66:2197–2200.

Knusel et al., (1990). Selective and nonselective stimulation of central cholinergic and dopaminergic development in vitro by nerve growth factor, basic fibroblast growth factor, epidermal growth factor, insulin and the insulin-like growth factors I and II. *J. Neurosci.*, 10:558–570.

Koutouzis et al., (1994). Systemic 3-nitropropionic acid: Long term effects on locomotor behavior. *Brain Research*, 646:242–246.

Lindvall et al., (1987). Transplantation in Parkinson's disease: two cases of adrenal medullary grafts to the putamen. *Ann. Neurol.*, 22:457–468.

Lindvall et al., (1990). Grafts of fetal dopamine neurons survive and improve motor function in Parkinson's disease. *Science*, 247:574–577.

Lindvall (1994). In *Functional neural transplantation*. (S. B. Dunnett, A. Bjorklund, Eds.), Raven Press, Ltd., New York, pp. 103–137.

Lindvall et al., (1990). Grafts of embryonic dopamine neurons survive and improve motor function in Parkinson's disease. *Science*, 247:547–577.

Martinez-Serrano et al. (1996). CNS-derived neural progenitor cells for gene transfer of nerve growth factor to the adult brain: complete rescue of axotomized cholinergic neurons after transplantation into the septum. *J. Neurosci.*, 15:5668–5680.

Mayer et al., (1993a). Basic fibroblast growth factor promotes the survival of embryonic ventral mesencephalic dopaminergic neurons-I. Effects in vitro. Neuroscience, 56:379–388.

Mayer et al., (1993b). Basic fibroblast growth factor promotes the survival of embryonic ventral mesencephalic dopaminergic neurons-II. Effects on nigral trasnplants in vivo. *Neurosci.*, 56:389–398.

Miao et al., (1996). A neurotrophic activity of sonic hedgehog promotes the survival of DA neurons. *Cell Transplant*, 5S-2,17.

Morales et al. (1996). Expression and tissue distribution of rat sulfated glycoprotein-1 (Prosaposin). *J. Histochem. Cytochem.*, 44:327–337.

Nikkhah et al., (1993). Platelet-derived growth factor promotes survival of rat and human mesencephalic dopaminergic neurons in culture. *Exp. Brain Res.*, 92:516–523.

O'Brien et al., (1994). Identification of prosaposin as a neurotrophic factor. *Proc. Natl. Acad. Sci. USA*, 91:9593–9596.

O'Brien (1985). Identification of the neurotrophic factor sequence of prosaposin. *FASEB*, 9:681–685.

Olson (1996). Toward trophic treatment in parkinsonism: a primate step. *Nature Med.*, 2:400–401.

Othberg et al., (1995). Specific effects of platelet derived growth factor (PDGF) on embryonic rat and human DA neurons in vitro. *Exp. Brain Res.*, 105:111–122.

Pakzaban et al., (1993). Increased proportion of Ache-rich zones and improved morphological integration in host striatum of fetal grafts derived from the lateral but not the medial ganglionic eminence. *Exp. Brain Res.*, 97:13–22.

Paxinos and Watson, (1984). The rat brain in stereotaxic coordinates" Sydney, Academic Press.

Pleasure and Lee (1993). Ntera-2 cells: a human cell line which displays characteristics expected of a human committed neuronal progenitor cell. *J. Neurosci. Res.*, 35:585–602.

Poulsen et al., (1994). TGFβ2 and TGFβ3 are potent survival factors for midbrain dopaminergic neurons. *Neuron*, 13:1245.

Rosenblad (1996). Glial cell line-derived neurotrophic factor increases survival, growth and function of intrastriatal fetal nigral dopaminergic grafts. Neurosci. 75:979–985.

Sagen et al., (1993). Transplants of immunologically isolated xenogeneic chromaffin cells provide a long-term source of pain-reducing neuroactive substances. *J. Neurosci.* 13:2415–2423.

Sanberg et al., (1996). Testis-derived Sertoli cells survive and provide localized immunoprotection for xenografts in rat brain. *Nature Biotech.*, 14:1692–1695.

Sanberg et al., (1997). Testis-derived Sertoli cells have a trophic effect on dopamine neurons and alleviate hemiparkinsonism in rats. *Nature Med.*, (submitted).

Sanberg, (Editor-in-chief) *Cell Transplantation*, Elsevier Science Publishers, New York, 1992–Present.

Sanberg et al., (1994). Cell transplantation for Huntington's disease R.G. Landes Co., Boca Raton, Fla., pp. 19–21.

Sauer and Brundin (1991). Effects of cool storage on survival and function of intrastrialtal ventral mesencephalic grafts. *Restor. Neurol. Neurosci.*, 2:123–135.

Sauer et al., (1994). Glial cell line-derived neurotrophic factor but not transforming growth factor β3 prevents delayed degeneration of nigral DA neurons following striatal 6-hydroxydopamine lesion. *Proc. Natl. Acad. Sci. USA.*, 92:8935–8939.

Sauer and Brudin (1991). Effects of cool storage on survival and function of intrastriatal ventral mesencephalic grafts. *Restor. Neurol. Neurosci.*, 2:123–135.

Selawry and Cameron, (1993). Sertoli cell-enriched fraction in successful islet cell transplantation. *Cell Transplant.*, 2:123–129.

Skinner (1993). Secretion of growth factors and other regulatory factors. In *The Sertoli Cell*, (Rusell, L. D. and Griswold, M. D. eds) Cache River Press, Clearwater, Fla., pp. 237–248.

Stromberg et al., (1993). Glial cell line-derived neurotrophic factor (GDNF) is expressed in the developing but not adult striatum and stimulates developing dopamine neurons in vivo. *Exp. Neurol.*, 124:401–412.

Takayama et al., (1995). Basic fibroblast growth factor increases DA graft survival and function in a rat model of Parkinson's disease. *Nature Med.*, 1:53–58.

Yoshimoto et al., (1995). Astrocytes retrovirally transduced with BDNF elicit behavioral improvement in a rat model of Parkinson's disease. *Brain Res.*, 691:25–36.

Wictorin et al., (1990). Reformation of long axon pathways in adult rat CNS by human forebrain neuroblasts. *Nature*, 347:556–558.

Zurn et al., (1994). Glial cell-line derived neurotrophic factor for motoneurones. *Neuroreport*, 6:113–118.

What is claimed is:

1. A method of enhancing the viability above control levels of cryopreserved cells, said method comprising the steps of:

adding sertoli cell conditioned medium produced by culturing $6\times10^5$ sertoli cells/cm$^2$ in a culture medium for 48 hours at 39° C. to cells to be cryopreserved.

2. The method as set forth in claim 1, wherein the cells to be cryopreserved include cells of the central nervous system, lymphocytes, hybridomas, fibroblasts, cells for gene therapy, fetal cells, myoblasts, endocrine cells, hepatocytes, or endothelial cells.

3. A method for enhancing the viability of cryopreserved cells, said method comprising the steps of:

co-culturing Sertoli cells and cells to be cryopreserved in media and cryopreserving together both the Sertoli cells and cells to be cryopreserved.

4. A method as set forth in claim 3 wherein said culturing step is further defined as co-culturing the Sertoli cells and cells to be cryopreserved for a period of time ranging from one hour to seven days.

5. A method of enhancing the viability of cryopreserved cells to be thawed, said method consisting essentially of the step of:

adding sertoli cell conditioned medium lacking sertoli cells as set forth in claim 1 to cryopreserved cells upon thawing.

* * * * *